(12) United States Patent
Biyikal et al.

(10) Patent No.: US 11,656,213 B2
(45) Date of Patent: May 23, 2023

(54) FLUORESCENT DYE FILMS FOR DETECTING NOX-BASED EXPLOSIVES IN THE AIR, IN SOLUTIONS, AND FROM WIPE SAMPLES

(71) Applicant: Institut Dr. Foerster GmbH & Co. KG, Reutlingen (DE)

(72) Inventors: Mustafa Biyikal, Berlin (DE); Knut Rurack, Berlin (DE)

(73) Assignee: Institut Dr. Foerster GmbH & Co. KG, Reutlingen (DE)

( * ) Notice: Subject to any disclaimer, the term of this patent is extended or adjusted under 35 U.S.C. 154(b) by 852 days.

(21) Appl. No.: 15/776,434

(22) PCT Filed: Nov. 16, 2016

(86) PCT No.: PCT/EP2016/077888
§ 371 (c)(1),
(2) Date: May 16, 2018

(87) PCT Pub. No.: WO2017/085137
PCT Pub. Date: May 26, 2017

(65) Prior Publication Data
US 2018/0372704 A1    Dec. 27, 2018

(30) Foreign Application Priority Data
Nov. 16, 2015 (DE) .......................... 102015119765.0

(51) Int. Cl.
*G01N 33/22* (2006.01)
*G01N 21/64* (2006.01)
(Continued)

(52) U.S. Cl.
CPC .......... *G01N 33/0057* (2013.01); *C09K 11/06* (2013.01); *G01N 21/6428* (2013.01);
(Continued)

(58) Field of Classification Search
CPC .. G01N 33/0057; G01N 33/22; G01N 33/227; C09B 57/008; C07C 211/54;
(Continued)

(56) References Cited

FOREIGN PATENT DOCUMENTS

| AT | 186348 B | 7/1956 |
|---|---|---|
| CN | 101088992 A | 12/2007 |

(Continued)

OTHER PUBLICATIONS

Costa, A.I. et al. "Substituted p-phenylene ethynylene trimers as fluorescent sensors for nitroaromatic explosives," Sensors and Actuators B 161 (2012) 251-260 (Year: 2012).*

(Continued)

*Primary Examiner* — Jennifer Wecker
*Assistant Examiner* — Michelle Adams
(74) *Attorney, Agent, or Firm* — Bachman & LaPointe, P.C.

(57) ABSTRACT

A detection reagent is disclosed in the form of a dye having the basic structure of a 4-(phenylethynyl)-phenyl-amine, a 4-(phenylethenyl)-phenyl-amine and/or a biphenylamine derivative. The dye can be used as detection reagent for nitroaromatics, nitroalkanes, nitroamines, nitrates, nitric acid, nitrous acid, nitrogen oxides, and additionally for sulphur dioxide (which is produced with the degradation of black powder). The dye can be an asymmetric triphenylamine derivative, which can lead to a fluorescence quenching, which can be used analytically in the case of electron abstraction.

30 Claims, 28 Drawing Sheets

(51) Int. Cl.
*G01N 33/00* (2006.01)
*C09K 11/06* (2006.01)

(52) U.S. Cl.
CPC .... *G01N 33/227* (2013.01); *C09K 2211/1007* (2013.01); *G01N 2021/6439* (2013.01)

(58) Field of Classification Search
CPC ... C07C 229/52; C07C 237/28; C07C 237/30; C07C 237/38; C07C 237/40
See application file for complete search history.

(56) References Cited

FOREIGN PATENT DOCUMENTS

| CN | 108473862 A | | 8/2018 |
|----|-------------|---|--------|
| DE | 19607253 A1 | | 8/1997 |
| JP | 0532587 A | | 2/1993 |
| JP | 05296992 A | | 11/1993 |
| JP | 08184867 A | * | 7/1996 |
| JP | 2013254135 A | | 12/2013 |
| JP | 2014172835 A | * | 9/2014 |
| JP | 2014218456 A | | 11/2014 |
| WO | 2008140635 A1 | | 11/2008 |
| WO | 2015050253 A1 | | 3/2017 |
| WO | 2015146965 | | 4/2017 |
| WO | 2017085137 A1 | | 5/2017 |

OTHER PUBLICATIONS

Bruice, Paula Yurkanis. Organic Chemistry, Third Edition. Upper Saddle River, New Jersey, Prentice Hall, 2001, Appendix II, pp. A-8 to A9. (Year: 2001).*

Shanmugaraju, S. et al. "p-Electron rich small molecule sensors for the recognition of nitroaromatics," Chem. Commun., 2015, 51, 16014; published on Oct. 8, 2015 (Year: 2015).*

Lin et al., "Meta versus para subsituent effect of organic dyes for sensitized solar cells", Journal of Photochemistry and Photobiology A: Chemistry 222 (2011), pp. 192-202.

Shi et al., "Synthesis, Structures, and Properties of Two Three-Dimensional Itietal-Organic Frameworks, Based on Concurrent Ligand Extension", Inorganic Chemistry, ACS Publications, (2012), pp. 6498-6506.

Davis et al., "FRET Detection of Proteins Using Fluorescently Doped Electrospun Nanofibers and Pattern Recognition", Langmuir, (2011), 27, pp. 6401-6408.

Donckele et al., "The 12 + 2I Cycloaddition-Retroelectrocyclization and [4+2] Hetero-Diels-Alder ileactions of 2-(Dicyanomethylene)indan-1,3-dione with Electron-Rich Alkynes: Influence of Lewis Acids on Reactivity", Organic Letters (2015), 17, pp. 3506-3509.

Cho et al., "The Benzil-Cyanide Reaction and its Application to the Development of a Selective Cyanide Anion Indicator", Journal of te American Chemical Society, (2008), 130, pp. 12163-12167.

Yang et al., "Zn (II)-Induced Ground-State π-Deconjugation and Excited-State Electron Transfer in N,N-Bis (2-pyridyl)amino-Substituted Arenes", The Journal of Organic Chemistry, (2004), 69, 3517-3525.

Boggian et al., "Efficient alkene synthesis on solid support using the Jutia-Kocienski coupling", Molecular Diversity (2010), 14, 847-853.

Che et al., "Diffusion-Controlled Detection of Trinitrotoluene: Interior Nanoporous Structure and Low Highest Occupied Molecular Orbital Level of Building Blocks Enhance Selectivity and Sensitivity", Journal of the American Chemical Society, (2012), 134, 4978-4982.

International search report for patent application No. PCT/EP2016/077888 dated Feb. 22, 2017.

Javad Safaei-Ghomi et al., "Sonochemically synthesis of arylethynyl linked triarylamines catalyzed by CuI nanoparticles: A rapid and green procedure for Sonogashira coupling", Ultrasonics Sonochemistry 22 (2015): 365-370.

Marcelo G. Vivas et al., "Experimental and theoretical study on the one-and two-photon absorption properties of novel organic molecules based on phenylacetylene and azoaromatic moieties" The Journal of Physical Chemistry B 116.50 (2012): 14677-14688.

Peter J. Holliman et al., "Ultra-fast co-sensitization and tri-sensitization of dye-sensitized solar cells with N719, SQ1 and triarylamine dyes." Journal of Materials Chemistry 22, No. 26 (2012): 13318-13327.

Jian Wang et al., "Synthesis of triphenylamine-modified arylates and ketones via Suzuki coupling reactions", Synthetic Communications, Feb. 28, 2011, 41(6): 832-40.

Alastair J. Florence et al., "Solving molecular crystal structures from laboratory X-ray powder diffraction data with DASH: the state of the art and challenges" Journal of applied crystallography, Apr. 1, 2005, 38(2):249-59.

Marietta O. Bautista et al., "Liquid-crystalline side chain polysiloxanes with 4-amino-4'-stilbenecarboxylic ester mesogens", Macromolecules, Jul. 26, 1993, (4):659-67.

Yuping Yuan et al., "Efficient Synthesis and Photosensitizer Performance of Nonplanar Organic Donor-Acceptor Molecules", Journal of nanoscience and nanotechnology, Aug. 1, 2015, 15(8):5856-66.

Shi-Chen Wang et al., Synthesis and Spectral Properties of Alkynyl Substituted Triphenylamines, 2015, Chinese Journal of Energetic Material, pp. 892-897.

Chinese Office Action dated Jan. 9, 2020 for Chinese Patent Application No. 201680077094.2.

McIlroy et al., "Two-Photon Photosensitized Production of Singlet Oxygen: Sensitizers with Phenylene-Ethynylene-Based Chromophores", JOC Article, vol. 70, (2005), pp. 1134-1146.

Mungkarndee et al., "Flourescense sensor array for identification of commercial milk samples according to their thermal treatments", Food Chemistry vol. 197, (2016) pp. 198-204.

European communication for patent application No. 16 805 323.9 dated Feb. 27, 2019.

Japanese office action for patent application No. 2018-524825 dated Jun. 4, 2019.

Canadian examination report for patent application No. 3,005,376 dated Apr. 13, 2021.

* cited by examiner

Table 1
The fluorescence quantum yields specified hereinafter of fluorescence indicator 4 were determined with use of the compound 2,2'-p-phenylenebis-(5-phenyloxazol) (POPOP) ($\varphi_f = 0.91$ in EtOH) as standard [8].

| Polarity | Solvent | $\lambda_{abs}$/nm | $\lambda_{em}$/nm | $\Phi_f$ |
|---|---|---|---|---|
| | Hexane | 367 | 394/410 | 0.67 |
| | Toluene | 375 | 425 | 1.00 |
| | CHCl$_3$ | 375 | 470 | 1.00 |
| | EtOH | 370 | 535 | 0.22 |
| | ACN | 367 | 545 | 0.56 |

FIG. 43

Table 2
The fluorescence quantum yields of fluorescence indicator 5 were determined as standard with use of the compound 2,2'-p-phenylenebis-(5-phenyloxazol), also referred to by its abbreviation POPOP, ($\varphi_f = 0.91$ in EtOH) [8].

| Polarity | Solvent | $\lambda_{abs}$/nm | $\lambda_{em}$/nm | $\Phi_f$ |
|---|---|---|---|---|
| | Hexane | 353 | 382/400 | 0.32 |
| | Toluene | 358 | 404 | 0.49 |
| | CHCl$_3$ | 358 | 428 | 0.67 |
| | EtOH | 355 | 470 | 0.65 |
| | ACN | 353 | 472 | 0.69 |

Tests on the long-term stability of sensor materials SM1-SM4 in open air and under argon

FIG. 44

FLUORESCENT DYE FILMS FOR DETECTING NOX-BASED EXPLOSIVES IN THE AIR, IN SOLUTIONS, AND FROM WIPE SAMPLES

BACKGROUND OF THE INVENTION

The invention lies in the field of detection of analytes comprising at least one NOx group and in particular relates to the detection of explosives and marker substances for explosives with the aid of optically measurable indicator layers.

Explosives that are used in practice and marker substances used to mark said explosives comprise compounds based on NOx. Compounds relevant for trace analysis are, for example, TNT (2,4,6-trinitrotoluene), DNT (2,4-dinitrotoluene and 2,6-dinitrotoluene), tetryl (2,4,6-trinitrophenylmethylnitramine), PETN (pentaerythritol tetranitrate), NG (nitroglycerin), EGDN (ethylene glycol dinitrate), RDX (hexahydro-1,3,5-trinitro-1,3,5-triazine), HMX (octahydro-1,3,5,7-tetranitro-1,3,5,7-tetrazocine), $NH_4NO_3$ (ammonium nitrate) and DMDNB (2,3-dimethyl-2,3-dinitrobutane—a marker substance). In the security, military and environment sectors, local detection of these compounds is of utmost practical importance. Most systems currently offered on the market for the detection of explosives are based on ion-mobility spectrometry (IMS), gas chromatography (GC), or Raman and infrared (IR) spectroscopic measurement technology. In particular, IMS (for example SABRE 4000, Smiths Detection/USA) and Raman apparatuses (for example FirstDefender™, Ahura/USA) have achieved commercial significance. Furthermore, the use of chemical methods based on chemiluminescence assays or molecularly interacting sensors, such as fluorescent conjugated polymers, known as amplifying fluorescent polymers (AFPs), have been described for the detection of explosives. Other compounds based on NOx that are relevant for trace analysis are pesticides for example, and the residues and degradation products (metabolites) thereof.

Besides the spatial requirement of the apparatuses, which typically operate in a stationary manner and thus require certain conditions to be satisfied, the known methods have the following further disadvantages:
   (i) IMS methods are based on a radioactive source and often have a disadvantageous drift behaviour.
   (ii) GC techniques require a carrier gas reservoir.
   (iii) Raman spectrometers typically require a connection to mains power, i.e. are not battery operated, and are susceptible to non-specific fluorescence.
   (iv) Laser-based methods are usually also not battery operated and are subject to matrix effects, which are often significant.

SUMMARY OF THE INVENTION

Against this background, a detection reagent, a method for detecting an analyte comprising a NOx group, a method for producing an analyte-sensitive layer, an analyte-sensitive layer, and the use of a detection reagent for monitoring a limit value of an explosive, all as disclosed herein, are proposed. Further embodiments, modifications, and improvements will become clear from the following description and the accompanying claims.

In accordance with a first aspect, a dye is proposed as detection reagent, the basic structure of said dye being selected from a 4-(phenylethynyl)-phenyl-amine, a 4-(phenylethenyl)-phenyl-amine and/or a biphenylamine derivative. The dye, which can be used as detection reagent for nitroaromatics, nitroalkanes, nitroamines, nitrates, nitric acid, nitrous acid, nitrogen oxides, and additionally for sulphur dioxide (which is produced with the degradation of black powder), thus has a basic structure according to one of formula images 1, 2 or 3:

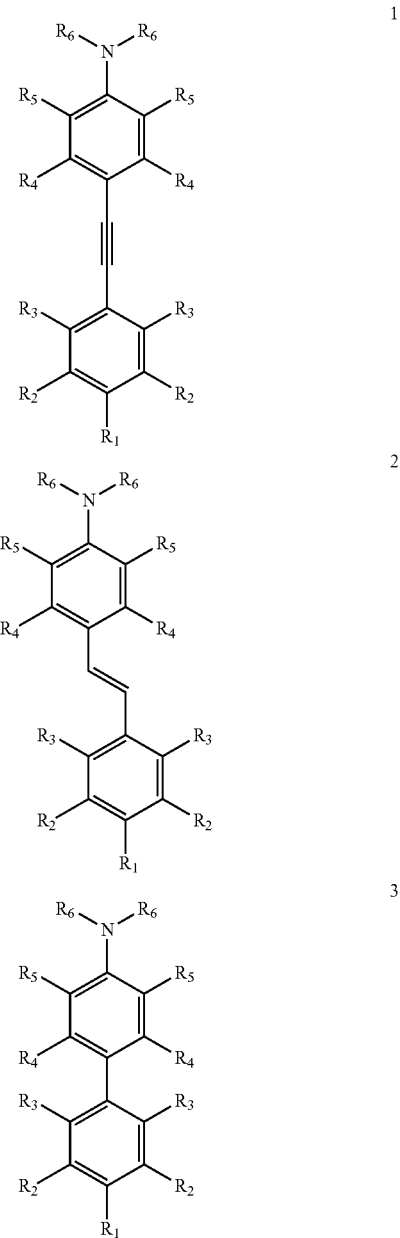

Here: $R_1=CO_2^-$, $PhCO_2^-$, $CO_2X$ or $PhCO_2X$ with (X=H, alkyl, vinyl, allyl, homoallyl, aryl) or
$R_1=C(O)NX_2$ or $PhC(O)NX_2$ with (X=H, alkyl, perfluoroalkyl, vinyl, allyl, homoallyl, aryl);
$R_2$, $R_3$, $R_4$ and $R_5$ independently of one another=H, F, alkyl, aryl; and
$R_6$=alkyl or aryl.

In accordance with preferred embodiments, $R_1$ stands for $CO_2Me$, for $C(O)N(Me)_2$, for $C(O)N(i-Pr)_2$, or for $PhC(O)N(Me)_2$, in particular for $PhC(O)N(i-Pr)_2$. For example, it is also preferred if $R_2$-$R_5$ each stand for H, in particular in combination with any one of the above-described preferred embodiments. It is also preferred if $R_6$ stands for a phenyl group, in particular in combination with the above-described preferred embodiments. It is also preferred if a triaryl group is covalently bonded to the para-substituted phenyl group by means of a triple bond.

It is particularly preferably proposed, for the detection of nitroaromatics, nitroalkanes, nitroamines, nitrates, nitric acid, nitrous acid, nitrous gases and sulphur dioxide, to use a 4-(phenylethynyl)-triphenylamine compound or (biphenylethynyl)-triphenylamine dye according to any one of formulas 4, 5 or 6 show below—that is to say an asymmetric triphenylamine derivative:

4

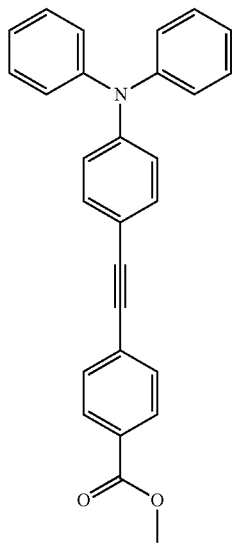

5

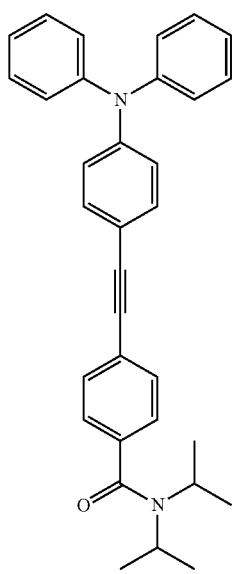

-continued

6

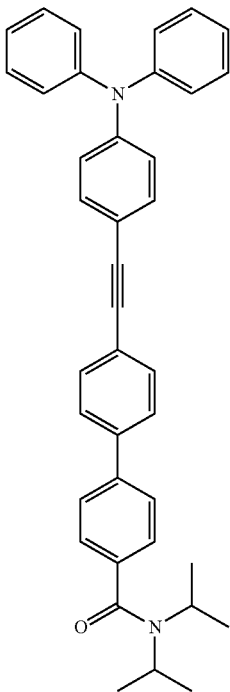

One of the three triphenylamino groups of these detection reagents is covalently bonded to a phenyl group by means of a triple bond, whereas two phenyl groups of the phenylamino group remain unsubstituted. The triphenylamino group covalently bonded by means of a triple bond to a phenyl group is again preferably substituted in the para position with an electron-withdrawing group. This results in the aforementioned asymmetry of the compound, which leads to a fluorescence quenching, which can be used analytically, in the case of electron abstraction.

Electron-rich groups such as amines (see formula 5) increase the electron density in the conjugated system, shift the emission signal of a relevant compound into the near UV range, and at the same time increase the sensitivity thereof to oxidation or air by atmospheric oxygen. In the presence of polar solvents (i.e. easily miscible with water), such as acetonitrile (ACN), a fluorescence signal of these compounds is shifted into the longer-wave range compared to a fluorescence signal of the same compound in a solvent of low polarity (high hydrophobicity, low miscibility with water), such as hexane (see Tables 1 and 2, FIGS. 43 and 44 respectively).

In the case of heavily electron-withdrawing groups, for example in the case of a nitrile group (CN), the electron density at the triphenylamine nitrogen decreases. This means that the energy of the acceptor (such as the explosive that is to be detected) is not sufficient for abstraction of an electron of the triphenylamine nitrogen, and therefore a much lower sensitivity of the indicator to the explosives or only a weak quenching of the fluorescence signal, which otherwise would be measurable with suitable excitation, will be observed.

For this reason, the electron-withdrawing group $R_1$—not only for compounds according to formulas 4 and 5, i.e. according to structural formula 1 in the broadest sense, but also for the dyes according to formulas 2 and 3—is advantageously selected such that the abstraction of an electron of the triphenylamine nitrogen in the presence of the NOx compounds is energetically favoured. As the dye interacts with the analyte comprising a NOx group, there is thus a fluorescence quenching. This makes it possible for example to reliably detect the aforesaid explosives (and marker substances thereof) by means of a spectroscopic measurement method, both qualitatively and—after calibration in the relevant temperature and humidity range—quantitatively. Among the measurement methods considered here, calorimetry is less suitable since it is one of the least sensitive techniques for trace analysis. By contrast, fluorescence-based measurement methods are typically at least 1000 times more sensitive. For this reason, preference is given to this measurement principle hereinafter.

In addition, a spectroscopic measurement with use of a liquid phase must preclude an interfering influence of the solvent on the analyte. For the explosives of interest here (primarily aromatic nitro compounds), the formation of strongly self-absorbing Meisenheimer complexes of the solvent (for example DMF, ACN) with the analyte (for example TNT) is known. Against this background a solid-phase-supported detection method is also preferred hereinafter.

Besides the sensitivity to the explosives mentioned at the outset, the electron-withdrawing group $R_1$ of indicator 1 in compounds according to formulas 4, 5 and 6 also has a strong influence on the molecular mobility of the fluorescence indicator when this is present at a solid/air phase boundary, for example at a polymer/air boundary. The molecules presumably aggregate at phase boundaries of this kind under the influence of the humidity acting as mobile phase on the (polymer) surface acting as stationary phase, such that their fluorescence is reduced on account of self-quenching.

If the indicators 4, 5 and 6 are applied directly to a substrate suitable for fluorescence measurement, for example to a glass surface, the intensity of measurable emission signals is not constant, and instead decreases continually. One reason for this appears to be a self-quenching. The problem of self-quenching was solved in the case of the previously known AFPs with the aid of sterically demanding iptycene units [3, 4], which prevent intermolecular interactions between apolar conjugated polymers on polar surfaces. Previously known concepts are thus based on the use of a fluorescent (conjugated) polymer.

In accordance with a second aspect, in contrast to this previously known approach, it is proposed here to stabilise the emission signal of a fluorescent molecule, specifically a compound 1, 2, 3, 4, 5 and/or 6, on a solid substrate by means of a non-fluorescent polymer film. In accordance with typical practical embodiments, this is achieved in that polymer films with an adapted polarity and layer thickness are constructed, for example on commercially obtainable carrier glass materials, for example on microscopy cover slips. The size or thickness of the selected substrate can be adapted to the measuring assembly used, for example a hand-held unit. The polarity, for example the wettability with water, can be adjusted here by the selection of functional groups of the polymer. The layer thickness in turn can be varied within wide ranges. At least one single molecule layer is preferably applied, wherein the thickness of the polymer layer is from 1 nm to 5 nm for detection of explosives which are non-volatile, and from 1 nm to 150 nm for detection of nitro compounds which are volatile, such as the marker DMDNB.

In accordance with a typical embodiment, it is proposed to equip a thin and non-fluorescent polymer film with a detection reagent which interacts specifically with a nitro compound that is to be detected and in so doing changes at least one fluorescence property. The polymer film provided with the detection reagent is expediently resistant under the measurement conditions for non-volatile explosives and is applied to a solid body, referred to here as a substrate, for example is applied to glass. In the presence of the NOx compound, a property of the detection reagent or of the polymer film equipped therewith that can be measured using a fluorescence-based optical method changes. In particular, it is proposed that the detection reagent is a fluorescent dye, comprising a tertiary amine according to the above-presented formulas bonded to at least one aryl. Accordingly, the terms detection reagent, dye, (fluorescence) indicator, and molecular probe will be used synonymously hereinafter in the relevant context. A polymer layer arranged on a substrate and equipped with at least one of the detection reagents will be referred to hereinafter as an analyte-sensitive layer.

For the detection of one or more non-volatile explosives and/or optionally one or more of the compounds used as marker substances of explosives or another NOx-containing analyte, it is proposed to determine the course over time of a fluorescence quenching of the detection reagent. The presence of the explosives and therefore the presence of a hazard potential is thus detected on the basis of a quenching of a fluorescence signal synchronously with a reversible (physico-chemical) interaction of the explosives (marker substances) with the detection reagent and/or on the basis of a renewed increase in fluorescence in the event of desorption of the explosive (marker substance) after previous quenching of the fluorescence of the detection reagent (i.e. during a regeneration). To this end, a course over time of a fluorescence intensity within a specific wavelength range is measured.

The NOx-containing analyte (explosive, marker substance, pesticide) can be present in the air, on the surface of an object (object surface), in aqueous or organic liquid, or the extract of a sample, for example a soil sample. Thermally induced sublimation, for example after breakdown of the analyte into nitrogen oxides, can also be used as a method for specific detection. The overshooting of a critical concentration (limit value) of the analyte in/on a sample indicates a hazard in accordance with the method. To this end, the qualitative detection of the NOx analyte can also be used alone in accordance with the method.

The sample can be transferred from an object surface to the analyte-sensitive layer either directly by flow (transfer) by means of explosive and/or marker substance vapours released from the surface, or can be detected firstly from the surface and applied to the analyte-sensitive layer with the aid of a transfer tool. The latter principle is known as the wipe sample method.

The polymer films can be constructed here on the substrate for example by means of spin coating on an untreated substrate surface starting from a polymer solution or by radical polymerisation of comonomers and cross-linkers on a surface covalently modified previously with 3-(trimethoxysilyl)propyl methacrylate, for example on a glass surface. In the latter case, "linked" glass is obtained. The embodiments described here by way of example are based on polymer chains covalently bonded to the glass as molecular monolayers or as polymer films, comprising polymer chains that are covalently bonded to the glass and that are cross-linked with one another at least in part. The detection reagent is then adsorptively bonded to the polymer film (FIG. 1-3). The fact that a polymer film equipped with detection reagent can be fully decolourised again by washing with organic solvents, such that there is no longer any fluorescence, but the solvent used for washing fluoresces, is considered to be proof of the bonding of the detection reagent to the polymer film based primarily on physico-chemical interactions.

Advantages of this embodiment lie in the fact that a polymer film adapted in respect of its polarity to the polarity of the particular detection reagent or a resultant strong interaction between the polymer material and the molecules of the detection reagent (dye) reduces the mobility of the latter at the air-polymer boundary. A stable emission signal can thus be measured in the case of optical excitation, adapted to the particular detection reagent, in the presence of an analyte (explosive or marker substance).

A further technical feature for setting a high sensitivity of the analyte-sensitive layer is the adaptation of the layer thickness of the polymer film carrying the molecular probe. Furthermore, the polymer material can be adapted in respect of its polarity, a mean chain length, and a length of the linkers (cross-linkers) used for the bridging of adjacent monomers to the chemical and physical properties of the explosive. This adaptation is used for the enrichment of volatile analytes (explosives, volatile decomposition products of (non-volatile) explosives and volatile markers). A reliable interaction (fluorescence quenching) and, as a result, an improved detection of the substance in question is achieved over an extended dwell time. The molar ratio of the monomers and a bifunctional reagent optionally used for cross-linking thereof determines a mean porosity of the obtained polymer layer for a given concentration of the radical former used for polymerisation and otherwise identical reaction conditions. For practical exemplary embodiments relating to the production of various polymer films used here by way of example, greater details are provided further below.

In particular, polymethacrylates have proven to be suitable polymers. The poly(benzyl acrylates) or poly(benzyl methacrylates) obtained starting from benzyl acrylate and benzyl methacrylate are cited merely as practical examples (see SM1 and SM2 described in greater detail hereinafter). The use of other monomers is also possible. In the radical polymerisation used, adjacent polymer chains can be directly cross-linked with one another. However, as presented by way of example for the sensor materials SM3 and SM4 also described later in greater detail, polymer chains cross-linked with one another with linkers, for example with bisacrylamide, can also be used to form a polymer layer. As already mentioned before, a wide range of different acrylates, acrylamide, or acrylamides, aryl acrylates, alkyl-substituted aryl acrylates, aryl acrylamides, or alkyl-substituted aryl acrylamides can also be cross-linked here with any cross-linking agents, for example a piperazine derivative or another bifunctional linker.

In accordance with a practical example, a thin, water-repelling polymer film is produced on a homogeneous glass surface for detection of a non-volatile NOx compound, starting from pure benzyl methacrylate (BMA), benzyl acrylate (BA), styrene, or derivatives thereof. Polymer films obtained in this way were coated with detection reagents 4 and 5 in accordance with exemplary embodiments described in greater detail further below. As will also be explained further below on the basis of specific examples, poly(benzyl methacrylate), poly(benzyl acrylate) and polystyrene solutions were for this purpose applied in apolar solvents, such as toluene, as a homogeneous layer to an untreated glass surface. In the second step, the detection reagent according to formula 4 or 5 is applied homogeneously in a polar solvent (for example isopropanol) to the polymer film. Once the organic solvent has vaporised, a homogeneously fluorescing analyte-sensitive layer is present.

The following advantages are provided here: the possibility of an inexpensive, simple and quick production of thin polymer films suitable for detection of explosives by fluorescence-based optical methods; a high oxidation stability, photostability and long-term stability of the resultant analyte-sensitive layers, comprising a polymer layer and detection reagent adsorptively bonded thereto; a high sensitivity of the analyte-sensitive layers to explosives based on NOx. In particular, a fluorescence signal measured on the analyte-sensitive layer (polymer film+detection reagent) changes in the presence of the explosive. As will be explained in greater detail further below, a thin polymer film which has been constructed on the substrate without an additional cross-linking agent has proven to be particularly suitable for non-volatile explosives. Nitro compounds with higher vapour pressure, by contrast, can be detected advantageously with the aid of analyte-sensitive layers comprising a thicker and porous polymer layer. For this purpose, suitable thicker polymer layers are preferably copolymer layers, which are formed from a first type of molecule (first monomer) and a second type of molecule, for example molecules having two terminal reactive groups (cross-linking agents). Due to the provided pores, these polymer layers appeared to be optically opaque, that is to say white.

The obtained polymers, i.e. poly(benzyl methacrylate), poly(benzyl acrylate) and polystyrene, can also be covalently anchored on the substrate surface. To this end, the glass surface is modified beforehand for example with 2-(trimethylsilyloxy)ethyl methacrylate ("linked" glass) and the polymer is covalently bonded by means of radical polymerisation. In the third step the dye 4 or 5 is then applied to the polymer film uniformly, for example by means of spin coating.

Advantages of this embodiment are the inexpensive, simple and quick production of polymer chains covalently anchored to the substrate, with the additional possibility to incorporate functional comonomers and thus adapt the polarity of the polymer chains to the polarity of the particular dye. Here, a polarity is advantageously set such that a strong interaction between the polymer chains and the dye is achieved and therefore the mobility of the dye molecules, which leads to the formation of aggregates, is limited, thus minimising the self-quenching of the fluorescence. This method ensures a high air stability, photostability and long-term stability of the dyes on the polymer film and a high sensitivity of the resultant analyte-sensitive layer for the detection of non-volatile explosives based on NOx.

Further advantages of the use of poly(benzyl methacrylate), poly(benzyl acrylate) and polystyrene as polymer matrix on glass are given by the fact that the corresponding hydrophobic polymer films are water-repellent and therefore contract in the presence of water. Due to the fact that polymer chains move closer towards one another as a result, the environment of the dye molecules becomes more apolar, whereby the fluorescence intensity of said molecules in the presence of an analyte increases and the fluorescence maximum shifts into the blue range of the spectrum (see Table 1, FIG. 43). If a non-volatile NOx compound, such as TNT, is present in the water vapour directed towards the analyte-sensitive layer, this compound thus remains on the polymer film, and a significant fluorescence quenching can be measured.

In addition, the shift and intensity of the fluorescence of the pure detection reagents the polymer-modified glass substrates can also be assessed as proof of the presence of the polymer layer on the glass: The detection reagent 4 applied to pure, chemically non-modified glass loses its fluorescence after a few hours in open air. The detection reagent 4 applied to the "linked" glass fluoresces relatively weakly ($\lambda_{max}$=470 nm), whereas the same detection reagent 4 applied in the same amount/area to a polymer-modified glass substrate demonstrates a pronounced and lasting fluorescence ($\lambda_{max}$=445 nm) (see FIG. 7-8). On account of the similar absorption intensities at $\lambda_{max}$=370 nm of the detection reagent 4 on the three differently modified glass substrate surfaces, the concentration of said detection reagent on non-modified glass substrate compared to polymer-modified glass substrate is only 1.2 times lower (FIG. 6). In addition, the fluorescence on "linked" glass under continued exposure ($\lambda_{max}$=370 nm) declines by 23% (FIG. 10), whereas it has proven to be stable (3% fluorescence quenching) on a polymer layer and under otherwise identical conditions (temperature, humidity). (FIG. 9).

Table 1, see FIG. 43
The fluorescence quantum yields specified hereinafter of fluorescence indicator 4 were determined with use of the compound 2,2'-p-phenylenebis-(5-phenyloxazol) (POPOP) ($\varphi_f$=0.91 EtOH) as standard [8].

In accordance with a further practical embodiment, a mixture of 1,4-bisacryloylpiperazine (BAP) with or without 2-hydroxyethyl methacrylate (HEMA) was polymerised on linked glass for detection of the marker substance DMDNB. The polymer matrix covalently bonded on the glass surface is coated in the second step with the dye 5 or 6 (FIG. 4).

Advantages result from the provision of a simple and quick production method for the thin polymer films, a high air stability, photostability and long-term stability of the detection reagents on the polymer film, and a high sensitivity to DMDNB by the enrichment thereof in the polymer material. Here, long-term stability is understood to mean the stability of the compound when stored under protective gas and away from light at room temperature.

Further advantages result from the transparency of the polymer films for the measurement of the fluorescence from the uncoated side of the glasses, and from the non-fluorescent and non-absorbing properties of the polymers poly(benzyl methacrylate), poly(benzyl acrylate) and polystyrene in the visible range of the spectrum, and from the uniform, good wettability of the glass surface for the polymers and the high stability of these polymers on the glass surface in open air.

It is similarly advantageous that the main absorption and fluorescence bands of the described triphenyl aminoalkynes lie in the visible spectral range. For this reason, it is possible to dispense with UV excitation of the probe for generation of a fluorescence signal. This results in reduced costs and in the possibility to provide a portable measuring apparatus, since UV excitation sources (at least still today) are much more costly, less stable and usually also bulkier than readers equipped with LEDs, for example.

Since both the polymer material and the glass absorb UV radiation, the excitation of the dyes on the polymer film is hereby facilitated.

Advantages of the detection of NOx compound, such as TNT, and advantages of the proposed detection method in air, in water, in organic solvents and on surfaces, are obvious. Advantages of the detection reagents used here relate to an uncomplicated sample preparation, which allows a direct and quick detection of a hazard potential directly and locally.

Further advantages result from the attained simplicity of the application and the low influence of ambient influences on the measurement. The advantages of the polymer films coated with fluorescent dyes are obvious: Precise measurements can be taken fault-free using the corresponding measuring device, even by untrained users. The polymer films can be produced reproducibly in high numbers, are resistant to the open air, and can be stored under protective gas indefinitely. The small influence of water and organic solvents, in combination with the corresponding measuring device, ensures a reliable measurement of air, water and wipe samples in a wide range of measurement situations.

In accordance with a further aspect, a method for detecting a NOx compound is proposed, wherein the detection is performed using a portable reader, preferably a portable reader that can be managed using one hand, which reader comprises a scanning device that measures at least at one defined wavelength.

Suitable readers are advantageously commercially available and are already used for various tests for detecting environmentally relevant chemicals. Continuous further development of portable apparatuses of this kind must be anticipated, such that on the one hand the sensitivity of the measurement methods that can be performed, but on the other hand also the range of spectroscopic parameters that can be reproduced and reliably evaluated ought to be increased potentially.

Accordingly, a method for detecting a NOx compound in the air is proposed, wherein the method comprises the following steps:
providing an analyte-sensitive layer, comprising a carrier material (molecule carpet, polymer) acting as solid phase with one of the previously described fluorescence probes;
measuring, in real time, the fluorescence and detecting a fluorescence property, in particular a fluorescence reduction of the analyte-sensitive layer with interaction between the analyte and the analyte-sensitive layer;

The method can optionally also comprise at least one of the following steps:
conducting a gas flow (for example air flow) potentially contaminated with a nitro compound towards the fluorescent layer, such that the portion of the carrier material is fully wetted by the air flow;
performing a qualitative analysis of the NOx compound on the basis of comparison values and/or curve characteristics and/or at least one previously detected regeneration phase with incident flow of analyte-free air or analyte-free water vapour onto the analyte-sensitive layer;
determining a concentration or a concentration range of the analyte (for example explosive) in the gas flow on the basis of a comparison value and/or a calibration curve, wherein the comparison value and/or the calibration curve were/was determined following interaction between the fluorescence probe and a known concentration of the analyte, for example in air.

The described measurement of the fluorescence quenching can be taken for example from the rear side of the substrate (i.e. from the non-coated side of the substrate). A corresponding measuring assembly presupposes an optically transparent substrate material. A measurement can also be taken from the coated side. The substrate (carrier material) and also the polymer film applied thereto therefore do not have to be transparent. If a suitable transparent substrate is used, for example glass, the fluorescence measurement can also be performed from an outer edge of the substrate on account of the light-guide properties of a substrate of this kind with reproducible coupling of the fluorescence light into the substrate. For example, this results in an advantageously compact measuring assembly.

In accordance with the approach that is conventional in the case of residue analysis, the original concentration of the analyte in question in the particular original sample (matrix+ analyte) can be determined following a calibration of the measurement signal for the concentration range in question with a currently ascertained measurement value (fluorescence quenching) from the proportions of the used sample volume (aliquot).

Accordingly, a method for detecting a NOx compound (explosive) from a solution, in particular from an aqueous or an organic solution, is proposed, the method comprising the following steps:
  providing an analyte-sensitive layer, comprising a carrier material acting as solid phase with one of the previously described fluorescence probes; measuring, in real time, the fluorescence reduction of the analyte-sensitive layer with interaction with the analyte using a suitable measuring assembly.

The method can optionally also comprise at least one of the following steps:
  vaporising the solution potentially contaminated with the analyte to be detected at a heated air inlet and conducting the resultant vapours with an air flow towards the fluorescent analyte-sensitive layer, such that a portion of the carrier material loaded with a fluorescence probe is fully wetted by the air flow;
  performing a qualitative analysis of the NOx compound on the basis of comparison values and/or curve characteristics and regeneration phases;
  determining a concentration or a concentration range of the analyte (explosive) in the solution on the basis of a comparison value and/or a calibration curve, wherein the comparison value and/or the calibration curve were/was determined following interaction of the fluorescence probe with a known concentration of the analyte.

In accordance with a further embodiment, a method for detecting a NOx compound, in particular a nitro-aromatic explosive material, on a surface is proposed. The method comprises the following steps:
  Loading a carrier material acting as solid phase with one of the previously described fluorescence probes and obtaining a fluorescent analyte-sensitive layer (indicator layer). This indicator layer is advantageously arranged on a rigid substrate and is exposed to an incident flow with a fluid (in particular a heated gas).
  Measuring the course over time of a fluorescence signal of at least a portion of the indicator layer with interaction of the analyte with the analyte-sensitive layer, in particular a reduction of the fluorescence of the indicator layer. As before, the fluorescence measurement can be performed both in transmission mode and as an epifluorescence measurement.

The method can optionally also comprise at least one of the following steps:
  Collecting analysis material from the surface using a wipe sample material, such that analysis material present on the surface is transferred to the wipe sample material.
  Heating the wipe sample material to a temperature >150° C. Conducting thermal sublimation and/or decomposition products of the wipe sample material released during the aforesaid heating process with a carrier gas flow (for example with a noble gas, a dry gas, or air) to the fluorescent indicator layer. Here, the portion of the carrier material loaded with the detection reagent is fully wetted by the carrier gas flow. As a result, the analyte introduced in the carrier gas flow can interact with the fluorescence probe.
  Performing a qualitative analysis of the NOx compound on the basis of previously recorded comparison values and/or curve characteristics or comparison values and/or curve characteristics stored in a database. A regeneration phase, i.e. a recovery of an initially at least partly quenched fluorescence under the action of a pure carrier gas (for example air) or with water vapour, can also be used in order to assess the material nature and/or concentration of the analyte in the carrier gas flow.
  Determining a concentration or a concentration range of the analyte (explosive) on the sample carrier on the basis of a comparison value and/or a calibration curve, wherein the comparison value and/or the calibration curve were/was determined following interaction of the fluorescence probe with a known concentration of the NOx-containing analyte, for example the explosive material or a marker substance of explosives.

Regardless of the type of the particular sample and the particular analyte-sensitive layer, a fluorescence measurement can comprise asynchronous excitation of one or more analyte-sensitive layers at different excitation wavelengths and/or at different emission wavelengths. One or more light sources can be used for excitation, for example laser, LED, OLED, or filament lamp.

The use of fluorescent conjugated polymers for detection of explosives by means of fluorescence quenching is known for example from U.S. Pat. No. 8,287,811 B1; U.S. Pat. No. 8,323,576 B2; U.S. Pat. No. 8,557,595 B2; U.S. Pat. No. 8,557,596 B2; CN 101787112 and [3-5]. The plurality of known detection methods for explosives based on NOx is based on the specific interaction between the AFP and the analyte with a high oxidation potential. In order to achieve a high sensitivity, thin layers of the AFPs are applied directly to the used substrate, for example to a glass.

The disadvantages of known detection methods based on conjugated polymers (AFPs) for the detection of explosives can be summarised in brief as follows:
  The existing cross-sensitivities of the fluorescent sensor materials currently considered to be technologically leading can lead to false alarms, for example also by sudden changes in the humidity or by interaction with substances that have a high oxidation potential not belonging to the group of explosives or marker substances. The existing cross-sensitivities hamper the overall efficacy or market acceptance of the sensor materials.
  This in turn has the disadvantage that the sensitivity for the explosive in question decreases. The field of use of AFPs of this kind as sensors for explosives based on NOx is therefore limited to relatively constant weather and environmental conditions.
  Besides an increased humidity and water, organic polar solvents miscible with water, and substances thermally producing water vapour, such as salts containing crystal water or thermally induced condensation reactions, can also increase the cross-sensitivity of the particular sensor material, or can reduce the specific sensitivity for the analyte.
  In order to attain a high sensitivity compared to the explosives, monomolecular layers of the conjugated polymers are necessary.
  The signal formation is based only on the interaction between the conjugated polymer and the analyte. The used carrier material, for example glass, demonstrates only a poor interaction with volatile analytes.

The marker substance DMDNB mandatorily contained since 1991 in commercially available explosives can only be detected in few cases with the aid of AFPs [7].

On account of the great variety of substance classes with their electronic or steric differences in the molecular structure and different properties (for example liquid/vapour pressure), the use of specifically adapted analyte-sensitive layers that enable a selective detection of different explosives is necessary for broad-spectrum detection—i.e. for the detection in parallel of different analytes in the same sample material.

An adaptation proposed here comprises the thickness and/or wettability of the polymer layer, which carries the molecular probe, to the volatility (vapour pressure) of an analyte, selected from one or more explosives and the marker used for marking thereof, for example DMDNB.

Accordingly, at least two functionalised, specific analyte-sensitive layers with different composition are used in order to be able to perform a classification (categorisation) of the explosives contained in the examined sample on the basis of the relative fluorescence signals of both layers via a pattern recognition, by measurement of specific characteristics and/or via the absolute or relative speed of the regeneration of the analyte-sensitive layers.

In the case of non-volatile explosives, such as TNT and RDX, the sensitivity of the analyte-sensitive layer is dependent above all on the layer thickness thereof. (FIGS. 29 to 31 show the fluorescence spectrum of SM1 before and after gassing with TNT at room temperature and the layer thicknesses of the corresponding polymer films).

The layer thickness of SM1 and SM2 is preferably between 1 and 5 nm. In order to make the layer visible under electron microscope, the polymer film was vapour-coated with gold and the break line was observed (FIG. 30). For SM3 and SM4 for detection of the marker DMDNB, polymer films with a porous, thicker layer (150-350 nm) are used for enrichment. The images recorded by electron microscope show that the surface of SM3 contains pores in the order of 50 nm, which enable the permeability of this material for volatile analytes, such as DMDNB (FIGS. 33 and 34). On account of the layer thickness of 150 nm, volatile analytes can therefore be enriched in this material (FIG. 35). In the case of SM4, the polymer surface comprises polymer particles on the basis of the recorded images assessed by electron microscopy. Measured layer thicknesses ranged from 160 to 350 nm (see FIG. 36).

In order to determine the dye density on the polymer films, the absorption was measured in a dilution series (in toluene) of the dyes 4, 5 and 6 with known concentration. On account of the linear behaviour of the absorption intensity relative to the dye concentration, the dye concentration on the polymer films could thus be determined. To this end, the polymer films coated with the corresponding dye were mixed with a certain amount of toluene and then the absorption of the solution was measured. The following dye concentrations were given for glass substrates with an area of 2.8 $cm^2$ for the sensor materials SM1-SM4: For SM1 and SM2 or poly(benzyl methacrylate) coated with dye 4 (75 pmol/$cm^2$); For SM1 and SM2 or poly(benzyl methacrylate) coated with dye 5 (30 pmol/$cm^2$); For SM3 or poly(1,4-bisacryloylpiperazine)/poly(2-hydroxyethyl methacrylate) coated with dye 6 (70 pmol/$cm^2$); For SM4 or poly(ethylene glycol dimethacrylate)/poly(2-hydroxyethyl methacrylate) coated with dye 5 (30 pmol/$cm^2$).

For TNT, which is non-volatile, a lower detection limit of 1.9 ng from a wipe sample was achieved. Here, an air flow conducted perpendicularly from the wipe sample towards the analyte-sensitive layer SM1 at a temperature of 120-150° C. triggered a mean fluorescence quenching of 20%. However, a fluorescence quenching of from 5 to 10% can already be reliably determined. This means that the lower detection limit of this analyte-sensitive layer actually achievable for TNT lies in the picogram range. The sensitivity can be optimised with the aid of optimised sample management (guidance of the air flow with the analyte towards the analyte-sensitive layer).

The lowest detectable concentration of TNT in the carrier gas flow (air, 120-150° C.) is 5 ppb. This was verified with the aid of a desiccator that provides a constant TNT concentration of an air sample. The constancy of this concentration was monitored by mass spectrometry.

Further non-volatile explosives such as PETN and ammonium nitrate form more volatile nitrates and nitrogen oxides when heated. These likewise demonstrate specific interactions with the analyte-sensitive layers and thus allow a specific detection.

The marker substance DMDNB is a volatile compound compared to TNT. The use of the proposed polymers as carrier layer of the detection reagent makes it possible to increase the dwell time of this compound on the analyte-sensitive layer by an enrichment of the particular volatile analyte and to thus reduce the detection limit into the ppb range. The layer thickness and the composition of the polymer film play a key role here. With increasing layer thickness of the analyte-sensitive layer, the sensitivity to the marker decreases, because the detection reagent can no longer be reached by the marker in the lower layers. With thin analyte-sensitive layers, by contrast, the analyte-sensitive layer in question likewise decreases. The optimal layer thickness of the analyte-sensitive layer for detection of the marker DMDNB is 130-170 nm (see FIG. 35).

Detailed Description of the Synthesis of used Detection Reagents

The detection reagents 4, 5 and 6 were synthesised as shown schematically in FIG. 1. All reagents originate from commercial manufacturers and were used without further purification. All air-sensitive and moisture-sensitive reactions were performed under protective gas (argon) in dry glass apparatuses. Triethylamine, diisopropylamine, dichloromethane and tetrahydrofuran were dried over molecular sieve (4 Å). The monomers for production of the polymer films were distilled or recrystallized in a high vacuum prior to their use. For analyses performed by thin-layer chromatography (TLC), Merck TLC plates, silica gel 60 F254 were used. The substances were made visible in UV light at 254 nm and 365nm. NMR measurements were performed with use of the signals of residues of protonated solvents as internal standard with an apparatus of the Bruker AV 400 or Bruker 600 type. Chemical shifts are specified here in ppm and coupling constants are specified in Hz. Mass spectra for characterisation of the detection reagents were detected using an "Exactive" Orbitrap mass spectrometer. The MALDI measurement for characterisation of the polymer layers of SM1 and SM2 was detected using the Autoflex III Smartbeam Bruker (FIG. 5). UV-vis absorption spectra were detected using a Specord 210 Plus spectrophotometer (Analytik Jena). Fluorescence measurements in solution and on polymer films were taken using a FluoroMax-4P spectrofluorometer (Horiba Jobin-Yvon, Bensheim). Solvents used for spectroscopic measurements were pure, accordingly (UV spectroscopic grade—Aldrich).

The starting material 4-ethynyl triphenylamine for production of the detection reagents or dyes 4 and 5 was produced in accordance with document [1], incorporated herein expressly by reference, or the synthesis procedure described therein.

Production of Detection Reagent 4

4-ethynyl triphenylamine (40 mg, 0.148 mmol) and methyl-4-iodobenzoate (50 mg, 0.191 mmol) were dissolved in dry THF/TEA (4 mL, 1:1) under protective gas and mixed with trans-dichlorobis(triphenylphosphine)palladium (12 mg, 0.016 mmol) and CuI (12 mg, 0.063 mmol) and stirred at room temperature. After 16 h the reaction mixture was diluted with ethyl acetate and mixed with HCl-acidic water (10%), and the raw product was extracted, dried over $Na_2SO_4$ and concentrated under reduced pressure. The raw product was purified by column chromatography on silica gel (cyclohexane:ethylacetate, 8:1). A yellowish solid was obtained (35 mg, 0.087 mmol, 59% yield).

$^1$H-NMR (500 MHz, $CDCl_3$) δ: 3.85 (s, 3H, $CH_3$), 6.93 (d, J=8.5 Hz, 2H), 7.00 (t, J=7.5 Hz, 2H), 7.05 (d, J=7.5 Hz, 4H), 7.21 (t, J=8.0 Hz, 4H), 7.30 (d, J=9.0 Hz, 2H), 7.48 (d, J=8.5 Hz, 2H), 7.93 (d, J=8.5 Hz, 2H). $^{13}$C-NMR ($CDCl_3$) δ: 52.2, 88.0 (q), 92.9 (q), 115.2 (q), 121.9, 123.7, 125.1, 128.4 (q), 129.0 (q), 129.4, 129.5, 131.3, 132.7, 147.0 (q), 148.3 (q), 166.6 (q). HRMS m/e 404,1650 (M+H)$^+$ (calculated for $C_{28}H_{21}NO_2$ 404,1645).

Production of 4-iodo-N,N-diisopropylbenzamide 4-iodobenzoyl chloride (500 mg, 1.88 mmol) was mixed in dichloromethane under protective gas at 0° C., dropwise, with diidopropylamine (0.8 mL, 5.69 mmol) and stirred at room temperature. After 16 h the reaction mixture was diluted with ethyl acetate and mixed with HCl-acidic water (10%), and the raw product was extracted, dried over $Na_2SO_4$ and concentrated under reduced pressure. The raw product was purified by column chromatography on silica gel (cyclohexane:ethylacetate, 5:1). A white solid was obtained (511 mg, 1.54 mmol, 82% yield). The spectra of the purified product matched the published data [2].

Production of Detection Reagent 5

4-ethynyl triphenylamine (54 mg, 0,200 mmol) and 4-iodo-N,N-diisopropylbenzamide (62 mg, 0.187 mmol) were dissolved in dry THF/TEA (4 mL, 1:1) under protective gas and mixed with trans-dichlorobis(triphenylphosphine)palladium (8 mg, 0.011 mmol) and CuI (8 mg, 0.042 mmol) and stirred at room temperature. After 16 h the reaction mixture was diluted with ethyl acetate and mixed with HCl-acidic water (10%), and the raw product was extracted, dried over $Na_2SO_4$ and concentrated under reduced pressure. The raw product was purified by column chromatography on silica gel (cyclohexane:ethylacetate). A yellowish solid was obtained (87 mg, 0.184 mmol, 98% yield).

$^1$H-NMR (500 MHz, $CDCl_3$) δ: 1.10 (br. s, 6H, $CH_3$), 1.44 (br. s, 6H, $CH_3$), 3.46 (br. s, 1H, CH), 3.74 (br. s, 1H, CH), 6.93 (d, J=8.5 Hz, 2H), 6.99 (t, J=7.5 Hz, 2H), 7.04 (d, J=7.5 Hz, 4H), 7.20 (m, 6H), 7.29 (d, J=8.5 Hz, 2H), 7.44 (d, J=8.5 Hz, 2H). $^{13}$C-NMR ($CDCl_3$) δ: 20.7, 45.9, 50.9, 88.0 (q), 90.7 (q), 115.7 (q), 122.2, 123.6, 124.0 (q), 125.0, 125.7, 129.4, 131.5, 132.5, 138.1 (q), 147.1 (q), 148.1 (q), 170.4 (q). HRMS m/e 473,2585 (M+H)$^+$ (calculated for $C_{33}H_{32}N_2O$ 473,2587).

Production of Detection Reagent 6

4-((4-(diphenylamino)phenyl)ethynyl)phenylboronic acid* (48 mg, 0.123 mmol) and 4-iodo-N,N-diisopropylbenzamide (40 mg, 0.121 mmol) were dissolved in THF/water (2.6 mL/0.9 mL) under protective gas and mixed with trans-dichlorobis(triphenylphosphine)palladium (8 mg, 0.011 mmol) and $Na_2CO_3$ (20 mg, 0.189 mmol) and stirred for 2 h at room temperature. After extraction with ethyl acetate and water, the raw product was dried over $Na_2SO_4$ and concentrated at reduced pressure. The raw product was purified by column chromatography over silica gel (cyclohexane:ethylacetate, 5:0.5). A yellow-brown solid was obtained (49 mg, 0.089 mmol, 74% yield). *tetrahedron 67 (2011) 6804-6811

$^1$H-NMR (500 MHz, $CDCl_3$) δ: 1.00 (br. s, 6H, $CH_3$), 1.35 (br. s, 6H, $CH_3$), 3.36 (br. s, 1H, CH), 3.73 (br. s, 1H, CH), 6.82 (d, J=9.0 Hz, 2H,), 6.87 (t, J=7.25 Hz, 2H), 6.93 (d, J=7.5 Hz, 4H), 7.09 (t, J=8.0 Hz, 4H), 7.19 (d, J=2.5 Hz, 2H), 7.21 (d, J=2.0 Hz, 2H), 7.39 (s, 4H), 7.42 (d, J=8.5 Hz, 2H). $^{13}$C-NMR ($CDCl_3$) δ: 20.7, 45.9, 50.9, 88.4 (q), 90.6 (q), 115.9 (q), 122.2, 122.9 (q), 123.5, 124.9, 126.2, 126.9, 127.0, 129.4, 131.9, 132.5, 137.9 (q), 139.7 (q), 140.6 (q), 147.1 (q), 147.9 (q), 170.7 (q). HRMS m/e 549,2908 (M+H)$^+$ (calculated for $C_{39}H_{36}N_2O_1$ 549,2900).

Polymer films equipped with detection reagents 4, 5 or 6 were produced in accordance with the steps presented schematically in FIGS. 2 to 4.

Activation and Functionalization or Linking of the Glass Substrate Surface

The glass substrates were heated in peroxymonosulfuric acid (40 mL $H_2O_2$ (30%) and 60 mL $H_2SO_4$) 2 h to 98° C. After washing with deionised water, the glass substrates were washed with acetone for 3 h in a Soxhlet apparatus. After drying (1 h at 150° C.) the cover slips were reacted in toluene (100 mL) with 3-(trimethoxysilyl)propylmethacrylate (6 mL, 25.2 mmol), triethylamine (1 mL, 7.2 mmol) and with the radical inhibitor 2,6-di-tert-butyl-4-methylphenol (50 mg, 0.23 mmol) for two days at room temperature. The glass substrates were then washed for 3 h with ethyl acetate in the Soxhlet apparatus and then stored under protective gas. The above-described method of activation, functionalization and linking is shown schematically in FIG. 2.

Production of poly(benzyl methacrylate), poly(benzyl acrylate) and polystyrene Films on the Glass Surface by Means of Spin Coating Benzyl methacrylate (600 μL, 3.5 mmol) was mixed with 3-(trimethoxysilyl)propyl-methacrylate (1 μL, 0.0042 mmol) in 1-hexanol (6 mL) with 2,2'-azobis(2,4-dimethylvaleronitrile) (ABDV) (12 mg, 0.05 mmol) and stirred for 17 h at 60° C. Once the solvent had vaporised, the polymer was washed with methanol and dried under vacuum. 200 mg of the polymer were dissolved in 2 mL toluene, and 10 μL of the solution were applied to a chemically untreated glass substrate by means of spin coating (312 rps). The polymer film was then washed at 312 rps with methanol (250 μL) and stored under protective gas. This production method can be seen in the schematic illustration in FIG. 3.

Production of Covalently Bonded poly(benzyl methacrylate), poly(benzyl acrylate) and Polystyrene Chains on the Glass Surface The linked glass substrates were mixed in 1-hexanol (6 mL) with benzyl methacrylate (600 μL, 3.5 mmol) and with 2,2'-azobis(2,4-dimethylvaleronitrile) (ABDV) (12 mg, 0.05 mmol) and heated for 3 h to 60° C. At the used high temperatures, however, other radical starters can also be used, such as 2,2'-azobis(2-methylpropionitrile) (AIBN) or 2,2,6,6-tetramethylpiperidin-1-oxyl (TEMPO). After the polymerisation, the glass substrates were washed for 1 h in a Soxhlet apparatus with ethyl acetate and then stored under protective gas. The method is shown schematically in FIG. 2.

Production of Polymer Films from 1,4-bisacryloylpiperazine and 2-hydroxyethyl methacrylate on the Glass Surface 1,4-bisacryloylpiperazine (520 mg, 2.68 mmol) was dissolved in 1-hexanol (2081 μL) at 60° C. 28 μL of the solution were then mixed with 1-hexanol (12 μL), HEMA (3 μL, 0.025 mmol) and 2,2'-azobis(2,4-dimethylvaleronitrile) (ABDV) (0.4 mg, 0.0016 mmol). After gassing with argon, 10 μL of the polymerisation mixture were applied between two linked glass substrates (Ø 19 mm, thickness no. 5 or 0.5 mm layer thickness) with flat surface, and the entire glass surface was wetted with the mixture. The glass substrates were then heated in 1-hexanol saturated atmosphere under protective gas for 1 h to 120° C. Once the glass substrates had been separated, the lower glass substrate was washed for 0.5 h in the Soxhlet apparatus with ethyl acetate. Once the polymer particles had been removed from the polymer film surface, this was washed again for 0.5 h in the Soxhlet apparatus with ethyl acetate and then dried in open air. The schematic illustration of these process steps is part of FIG. 4.

Production of Polymer Films from Ethylene Glycol Dimethacrylate and 2-hydroxyethyl methacrylate on the Glass Surface Ethylene glycol dimethacrylate (3 μL, 0.016 mmol) and 2-hydroxyethyl methacrylate (7 μL, 0.058 mmol) were mixed in 1-hexanol (40 μL) with 2,2'-azobis(2,4-dimethylvaleronitrile) (ABDV) (0.4 mg, 0.0016 mmol). After gassing with argon, 1 μL of the polymerisation mixture was applied between two linked glass substrates (Ø 19 mm, thickness no. 5 or 0.5 mm layer thickness) with flat surface, and the entire glass surface was wetted with the mixture. The glass substrates were then heated in 1-hexanol saturated atmosphere under protective gas for 1 h to 120° C. Once the glass substrates had been separated, the lower glass substrate was washed for 0.5 h in the Soxhlet apparatus with ethyl acetate. Once the polymer particles had been removed from the polymer film surface, this was washed again for 2 h in the Soxhlet apparatus with ethyl acetate and then dried in open air. The schematic illustration of these process steps is part of FIG. 4.

The production of specific properties and the use of four sensor materials SM1-SM4 will be described hereinafter.

Production of the Sensor Material SM1 for Detection of Non-Volatile Explosives and Nitro Aromatics For production of sensor material SM1, dye 4 or 5 was dissolved in 2-propanol (c=0.56 mM) in an ultrasonic bath and then at 60° C. The glass substrates (Ø 3-19 mm, 0 13-0.5 mm layer thickness) covalently bonded with poly(benzyl methacrylate), poly(benzyl acrylate) and polystyrene were accelerated with the spin coater to 312 rps, washed with 100 μL 2-propanol, and then 5 μL of the dye solution was applied, and the glass substrate was dried for one minute with the aid of the spin coater. The sensor material was then dried for 24 h in open air and then stored under protective gas away from light.

Production of Sensor Material SM2 for Detection of Non-Volatile Explosives and Nitro Aromatics For production of sensor material SM2, dye 4 or 5 was dissolved in methanol (c=0.56 mM) in an ultrasonic bath and then at 60° C. The glass substrates coated with poly(benzyl methacrylate), poly(benzyl acrylate) or polystyrene were accelerated on the spin coater to 312 rps, washed with 250 μL of methanol, and then 5 μL of the dye solution were applied and the glass substrate was dried for one minute with the aid of the spin coater. The sensor material was then dried for 24 h in open air and stored under protective gas and away from light.

Production of Sensor Material SM3 for Detection of DMDNB and Nitro Aromatics

For production of sensor material SM3, dye 5 or 6 was dissolved in toluene (c=0.56 mM). The glass substrates coated with a poly(1,4-bisacryloylpiperazine) film (and poly (2-hydroxyethyl methacrylate)) were accelerated on the spin coater to 312 rps, and 5 μL of the dye solution were applied, and the glass substrate was dried for one minute with the aid of the spin coater. The sensor material was then dried for 24 h in open air and stored under protective gas and away from light.

Production of Sensor Material SM4 for Detection of DMDNB, TNT and Nitro Aromatics.

For production of sensor material SM4, dye 5 or 6 was dissolved in toluene (c=0.56 mM). The glass substrates coated with poly(ethylene glycol dimethacrylate) and poly (2-hydroxyethyl methacrylate) were accelerated on the spin coater to 312 rps, and 5 μL of the dye solution were applied, and the glass substrate was dried for one minute with the aid of the spin coater. The sensor material was then dried for 24 h in open air and stored under protective gas and away from light.

Production of the Reference Material for SM1

For production of the reference material, 1 μL of dye solution 4 was mixed in 2-propanol (c=5.6 mM) with benzyl methacrylate (20 μL, 0.117 mmol), ethylene glycol dimethacrylate (30 μL, 0.16 mmol) and with 2,2'-azobis(2,4-dimethylvaleronitrile) (ABDV) (0.75 mg, 0.003 mmol). 0.5 μL of the solution was polymerised between two linked glass substrates (glass 1=Ø 19 mm, Ø 13-0.5 mm layer thickness; glass 2=Ø 5 mm, 0.13 mm layer thickness) and polymerised for 20 minutes at 150° C.

Test on the Photostability of Sensor Materials SM1-SM4 during the Measurement.

Tests on the photostability of sensor materials SM1 to SM4 were performed in open air with the aid of a Fluoro-Max-4P spectrofluorometer. Once the fluorescence spectrum has been recorded (excitation $\lambda_{exc}$=365 nm, slit 1.5 nm, emission $\lambda_{em}$=375-600 nm, slit 5 nm) the sensor materials were irradiated at an excitation wavelength of $\lambda_{exc}$=365 nm with a slit of 2.5 nm for 5 minutes, and the changes to the emission maximum were recorded. The fluorescence spectrum was then recorded again (excitation $\lambda_{exc}$=365 nm, slit 1.5 nm, emission $\lambda_{em}$=375-600 nm, slit 5 nm) (see FIGS. 6 and 7).

The excellent photostability of the detection reagents on the corresponding polymer films was demonstrated in particular by the reduction of the emission maximum after 5 minutes continuous irradiation by 1.5-3% with the fluorescence spectrometer with a higher fluorescence excitation intensity at a wavelength of 365 nm or 370 nm with a slit of 2.5 nm (FIG. 9, 15, 18, 22, 25). In the case of SM1 the emission signal of detection reagent 4 on the poly(benzyl methacrylate) film remains constant even over several days in open air at room temperature (FIG. 40).

The high photostability of detection reagent 4 on hydrophobic surfaces and of detection reagent 5 on polar surfaces is complemented by the high quantum yields of these molecular probes.

Representative spectra and spectroscopic data of 4 and 5 in solvents and polymers of different polarity are summarised in Tables 1 and 2, FIGS. 43 and 44, and in FIGS. 6-25, 29 and 31.

Table 2, FIG. 44

The fluorescence quantum yields of fluorescence indicator 5 were determined as standard with use of the compound 2,2'-p-phenylenebis-(5-phenyloxazol), also referred to by its abbreviation POPOP, ($\varphi_f$=0.91 in EtOH) [8].

Tests on the long-term stability of sensor materials SM1-SM4 were performed with the aid of the FluoroMax-4P spectrofluorometer. Once the fluorescence spectrum had been recorded (excitation $\lambda_{exc}$=365 nm, slit 0.5 nm, emission $\lambda_{em}$=375-600 nm, slit 5 nm) for the sensor materials, these were stored at room temperature in open air (FIG. 9) or argon (FIG. 11) away from light. The measurement was repeated at specific time intervals.

An aggregate forming of the probes or oxidation of the probes by atmospheric oxygen in the matrix can be ruled out on the basis of the present experimental findings, since the spectra did not change after 24h in open air or with irradiation and heating in open air (FIG. 9). Nevertheless, the sensor materials are advantageously stored under an inert gas, for example under argon, until their time of use, in order to avoid passivation of the sensitive layer (FIG. 11).

Tests on the Interactions of Sensor Materials SM1-SM4 with Humidity and Water and/or Water Vapour.

The detection of NOx explosives with AFPs is greatly hindered, as is known, by a sudden change to the humidity and by moist wipe samples. In order to avoid the effect of water competing with the explosives, it is proposed to use hydrophobic polymers, such as poly(benzyl methacrylate), poly(benzyl acrylate) and polystyrene in sensor material SM1 and SM2. By means of a complexing of the detection reagents by the polymer chains, the mobility of fluorescence probes 4 and 5 proposed here can be limited, even in the presence of water vapour at a water temperature of 40-90° C., and it is thus possible to prevent the TNT detection limit of 5% fluorescence quenching from being reached (see the table in [0084]).

As a result, when introducing water vapour from the surface of a 40-60° C. water sample onto the sensor material, a maximum signal reduction of 2.7% is observed, measured 1 cm above the water surface, which does not reach the lower detection limit (5% signal reduction), and this recovers quickly (see FIG. 37), in contrast to the recovery period of the sensor materials of TNT (FIG. 26). Results are summarised in Table 3 below.

TABLE 3

| Water temperature [° C.] | Signal reduction [%] |
|---|---|
| 40 | 0.3-0.8 |
| 50 | 1.3-2.2 |
| 60 | 1.6-3.4 |
| 65.5 | 1.0-2.7 |
| 67.3 | 0.2-2.5 |
| 70-90 | Fluorescence increase |

When introducing water vapour from the surface of a 70-90° C. water sample onto the sensor material, measured 1 cm above the water surface, only a signal increase is observed, by contrast. In combination with the dilution of detection reagent 4 on the polymer surface of SM1 (75 pmol/cm$^2$), the self-quenching effect is thus ruled out. For the sensitive detection of explosives, however, high quantum yields of the detection reagent are necessary for this concentration range. Precisely these yields are offered by fluorescence sample 4 in a hydrophobic environment (see Tables 1 and 2, FIGS. 43 and 44).

Sensor material SM3 demonstrates a quenching of the measurement signal, which recovers quickly again, only in the case of a temporary humidity increase, for example through vaporisation of pure water in the immediate vicinity of the analyte-sensitive layer SM3. In the presence of the marker substance DMDNB, the sensor material SM3 likewise demonstrates a fluorescence quenching, but it recovers slowly depending on the polymer material composition (FIG. 28).

This unusually long recovery phase of sensor material SM3 from a volatile compound, such as DMDNB, is presumably attributable to the fact that the polymer contains pores, which can absorb the marker substance DMDNB, If, however, during the recovery phase, water vapour is conducted onto the sensor material SM3 contaminated with DMDNB, the measurement signal recovers within a few seconds and reaches the baseline again. The regenerated sensor material can then be used again for the next measurement (see FIG. 28).

The present results justify the conclusion that the water vapour forces the marker substance DMDNB from the pores of the sensor material SM3. On account of the high temperatures (>150° C.) in the air passage system, the water in the polymer material vaporises, which brings about a regeneration of the measurement signal.

Against this background, the proposed fluorescence dyes on the polymer films adapted accordingly in respect of their polarity offer a possibility for the selective detection of explosives based on NOx in air, in water, in organic solvents, and on surfaces. In particular, the use of hydrophobic poly(benzyl methacrylate) or polystyrene films on glass substrates equipped with the aforesaid molecular probes 4 or 5 for use in a robust hand-held device for the detection of explosives, such as TNT, tetryl, PETN, NG, EGDN, RDX, HMX, NH$_4$NO$_3$ and the marker DNT is proposed. The use of the hydrophilic poly(1,4-bisacryloylpiperazine)/2-hydroxyethyl methacrylate film on a glass substrate equipped with molecular probe 6 in a robust hand-held device for the detection of the volatile markers DMDNB, DNT and for the detection of explosives, such as PETN, NG, EGDN, NH$_4$NO$_3$ is proposed.

BRIEF DESCRIPTION OF THE DRAWINGS

The accompanying figures show embodiments and shall be used together with the description to explain the principles of the invention. The elements in the drawings are shown relative to one another and not necessarily true to scale. Like reference signs denote similar parts accordingly.

FIG. 43 presents Table 1 as referred to throughout the specification.

FIG. 44 presents Table 2 as referred to throughout the specification.

DETAILED DESCRIPTION OF THE MEASUREMENT METHOD

Figure 1:
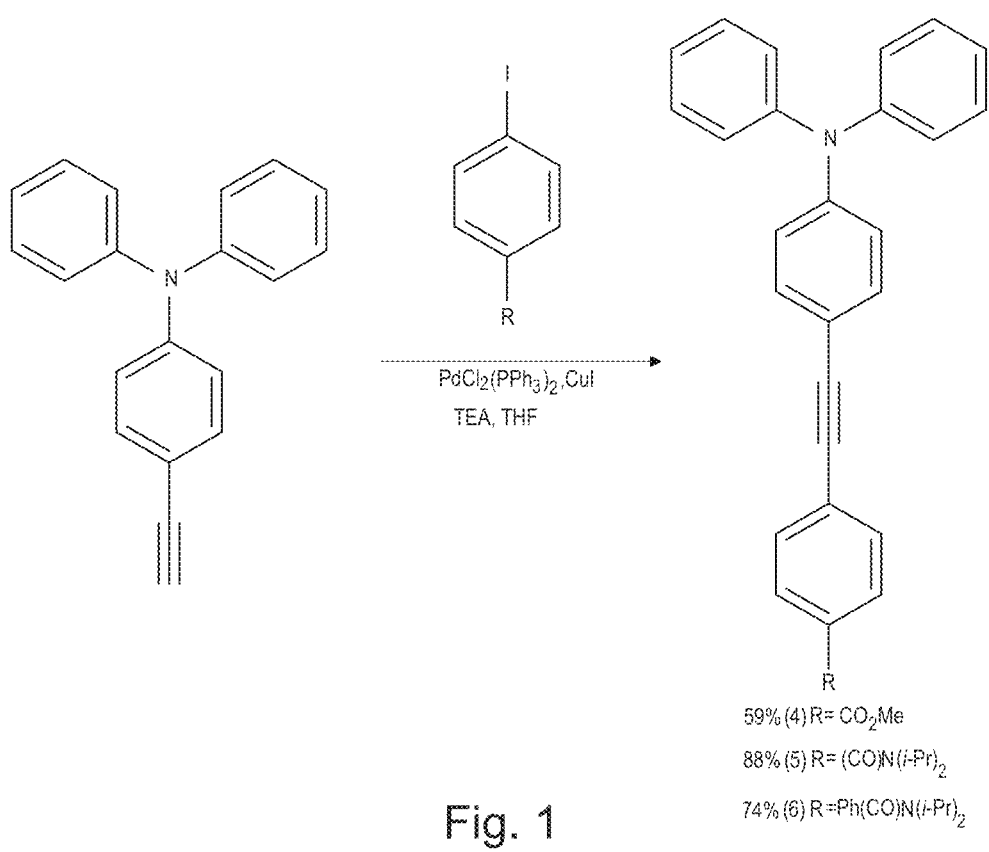
FIG. 1 shows a synthesis schema presenting fluorescence probes 4, 5 and 6.
Figure 2:
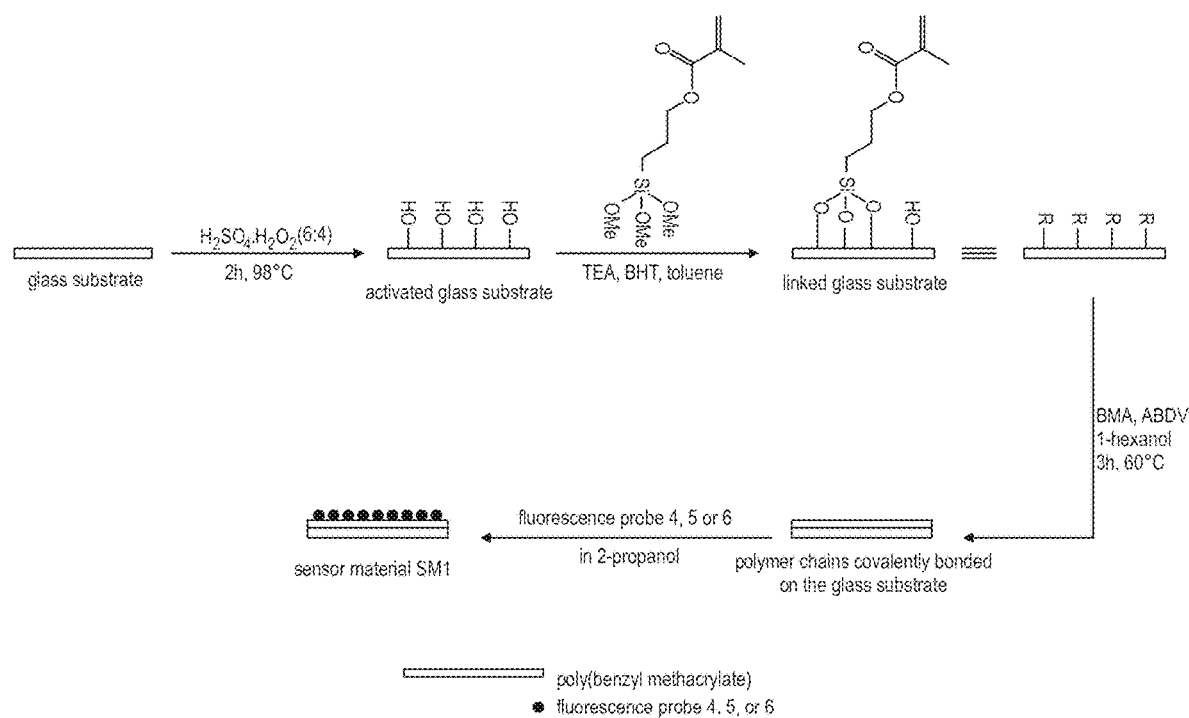
FIG. 2 schematically shows a method for producing the sensor material SM1, the covalent bonding of the polymer chains with the linked glass substrates, and the coating of the polymer chains covalently bonded to the glass substrate with the fluorescence probes 4, 5 and 6.
Figure 3:
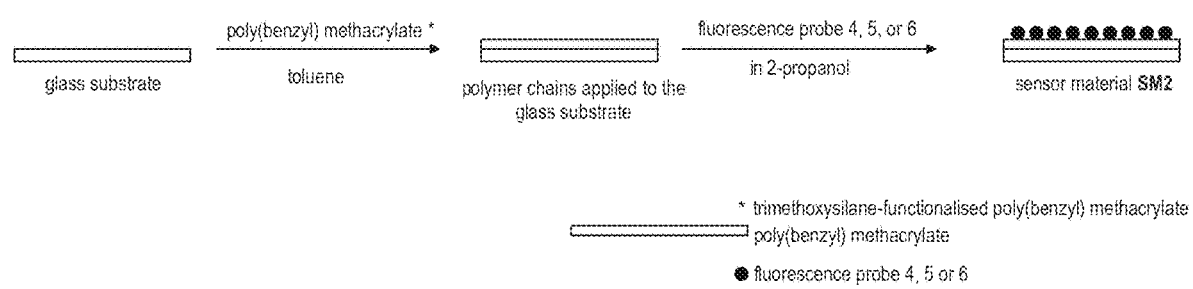
FIG. 3 schematically shows a method for producing the sensor material SM2, the production of the glass substrates coated with poly(benzyl methacrylate) by means of spin coating, and the coating of the polymer chains applied to the glass substrate with the fluorescence probes 4, 5 and 6.
Figure 4:
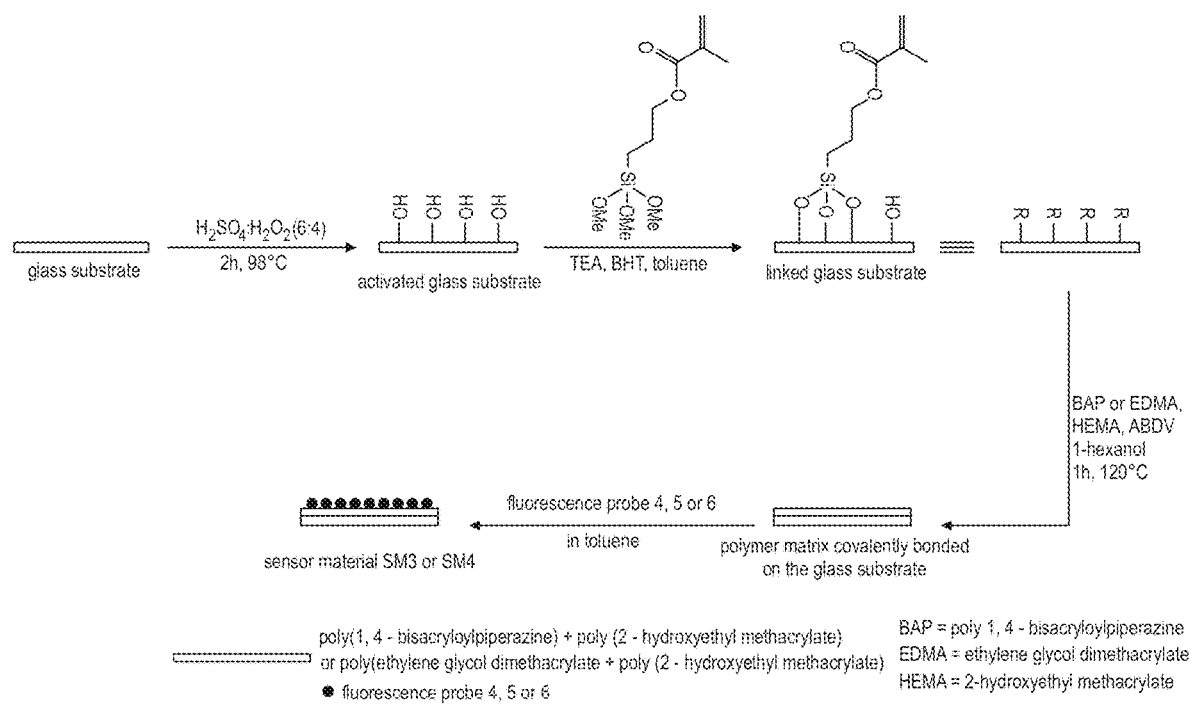
FIG. 4 schematically shows a method for producing the sensor materials SM3 and SM4, comprising the production of the linked glass substrates, the covalent bonding of the cross-linked polymer with the linked glass substrates, and the coating of the polymer matrix covalently bonded on the glass substrate with the fluorescence probes 4, 5 and 6.
Figure 5:
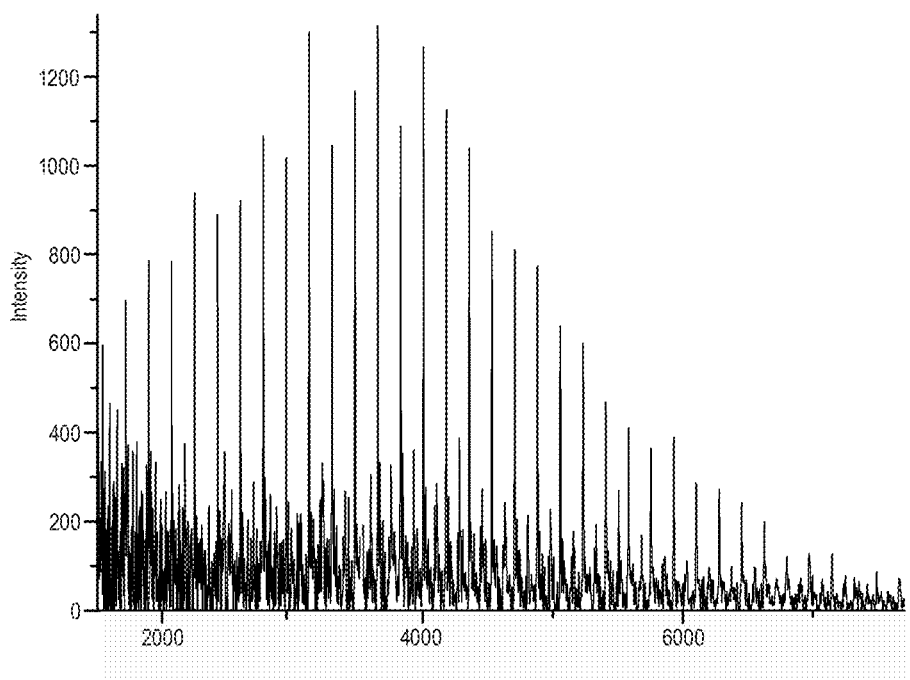
FIG. 5 shows Maldi spectra of poly(benzyl methacrylate) from the 1-hexanol solution of the polymer produced during the substrate treatment.
Figure 6:
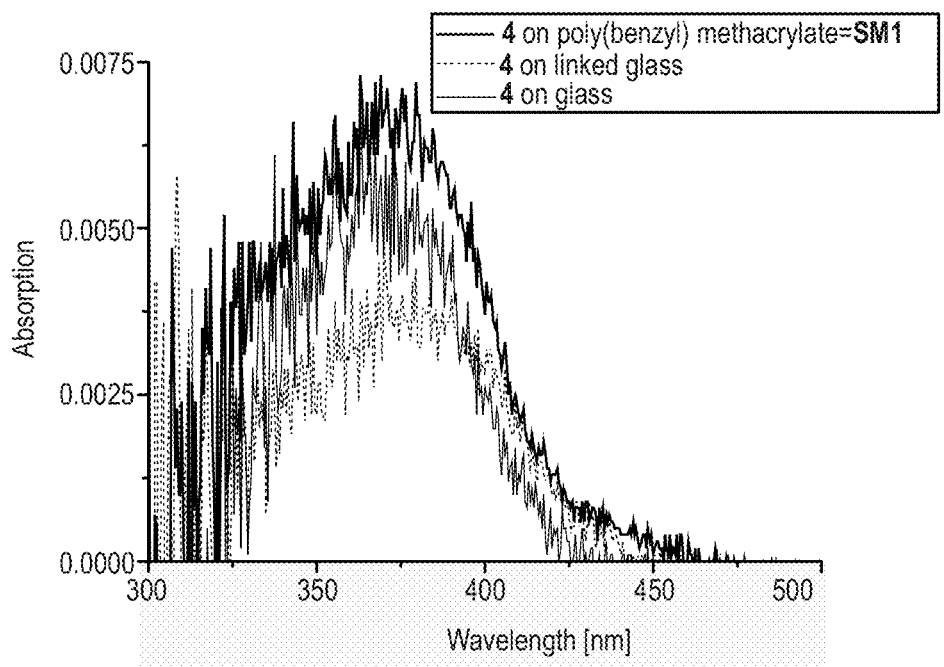
FIG. 6 shows the absorption spectrum of detection reagent 4 on chemically untreated glass, on "linked" glass, and on glass coated by poly(benzyl methacrylate) (SM1).
Figure 7:
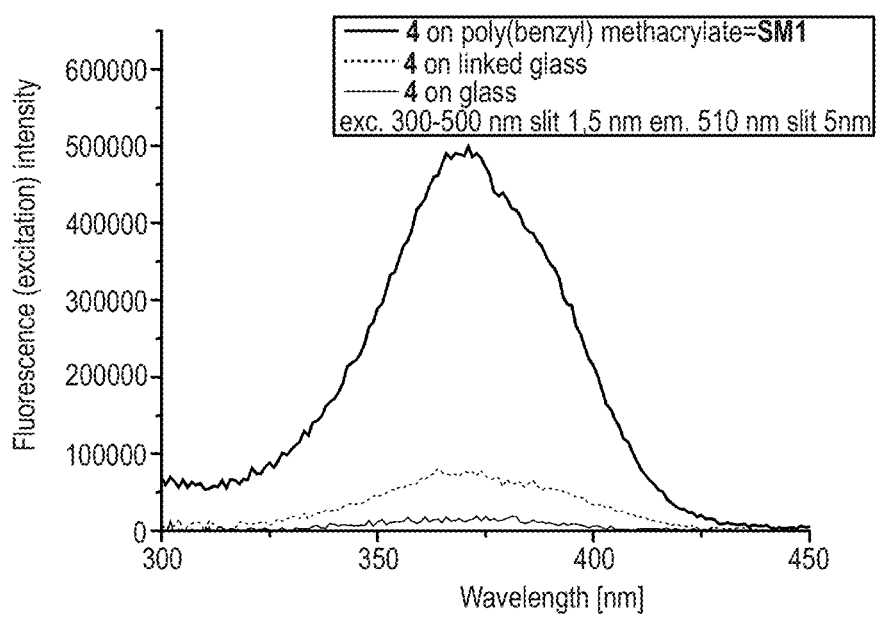
FIG. 7 shows the fluorescence excitation spectrum of detection reagent 4 on chemically untreated glass, on "linked" glass, and on glass coated by poly(benzyl methacrylate) (SM1).
Figure 8:
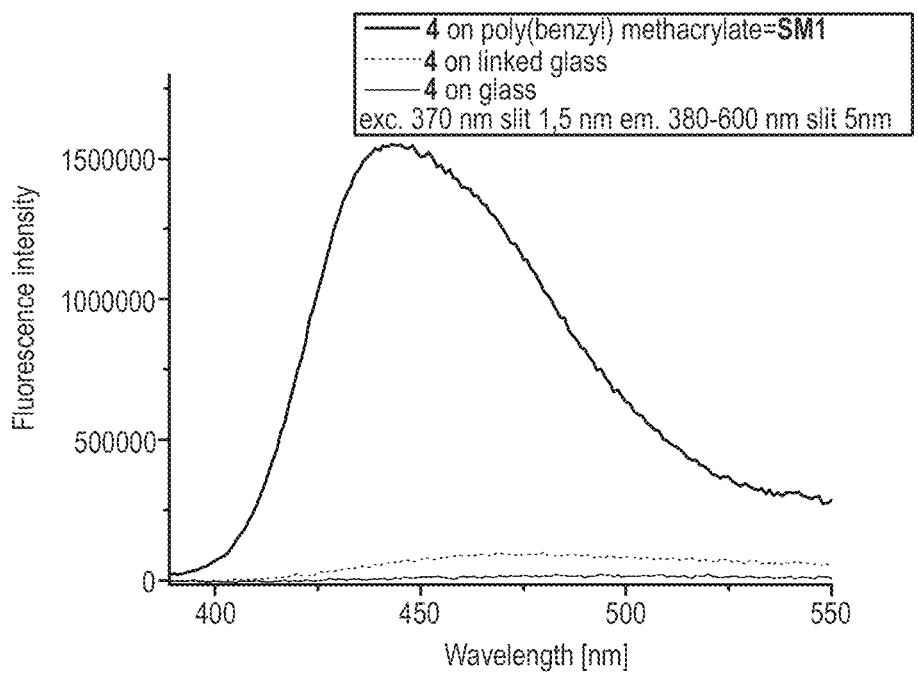
FIG. 8 shows the fluorescence spectrum of detection reagent 4 on chemically untreated glass, on "linked" glass, and on glass coated by poly(benzyl methacrylate) (SM1).
Figure 9:
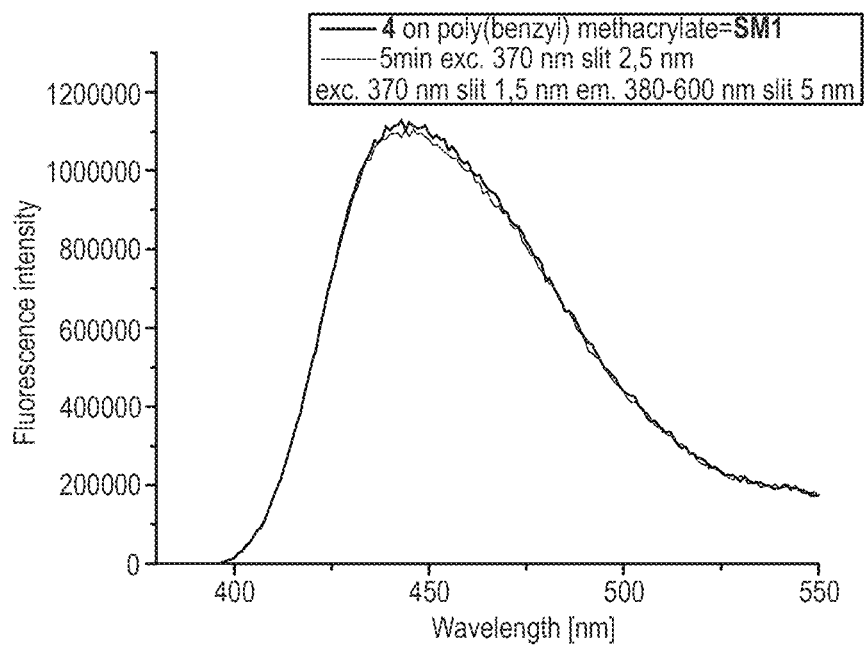
FIG. 9 shows results or the fluorescence spectrum of tests on the photostability of detection reagent 4 on glass coated by poly(benzyl methacrylate) (SM1) before and after continuous irradiation at higher excitation intensity.
Figure 10:
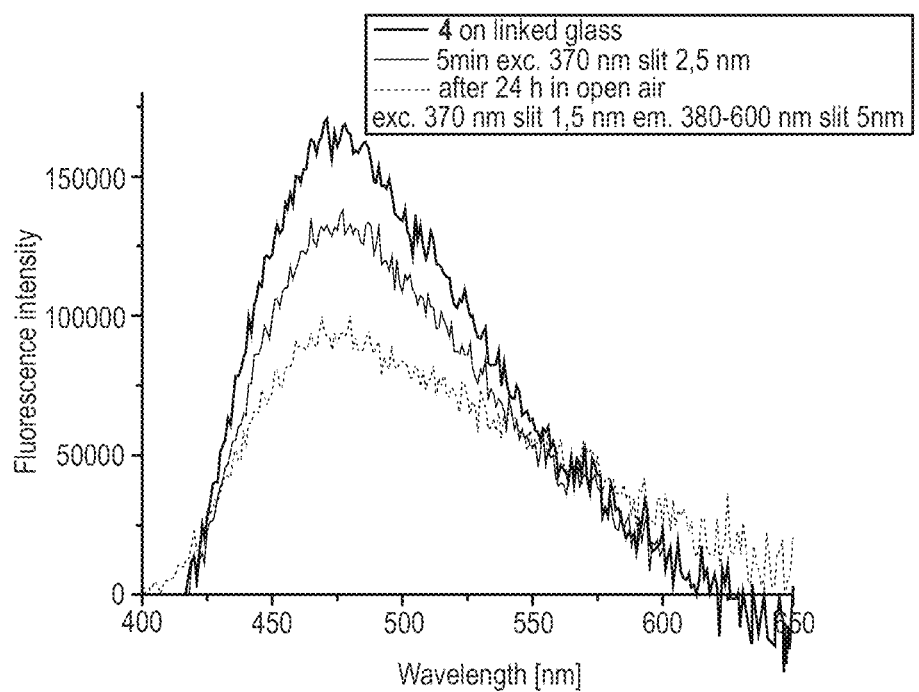
FIG. 10 shows results or the fluorescence spectrum of tests on the photostability and air stability of detection reagent 4 on "linked" glass before and after continuous irradiation at higher excitation intensity and after subsequent storage in open air for 24 hours.
Figure 11:
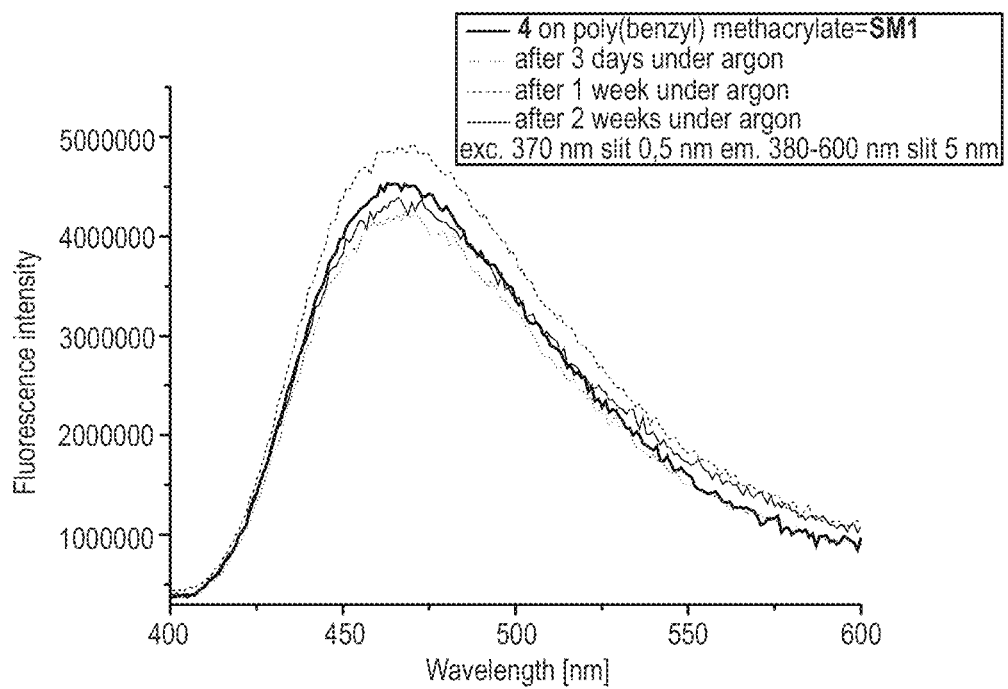
FIG. 11 shows results or the fluorescence spectrum of tests on the long-term stability of detection reagent 4 on glass coated by poly(benzyl methacrylate) (SM1) under argon protective gas after three days, after one week, and after two weeks.
Figure 12:
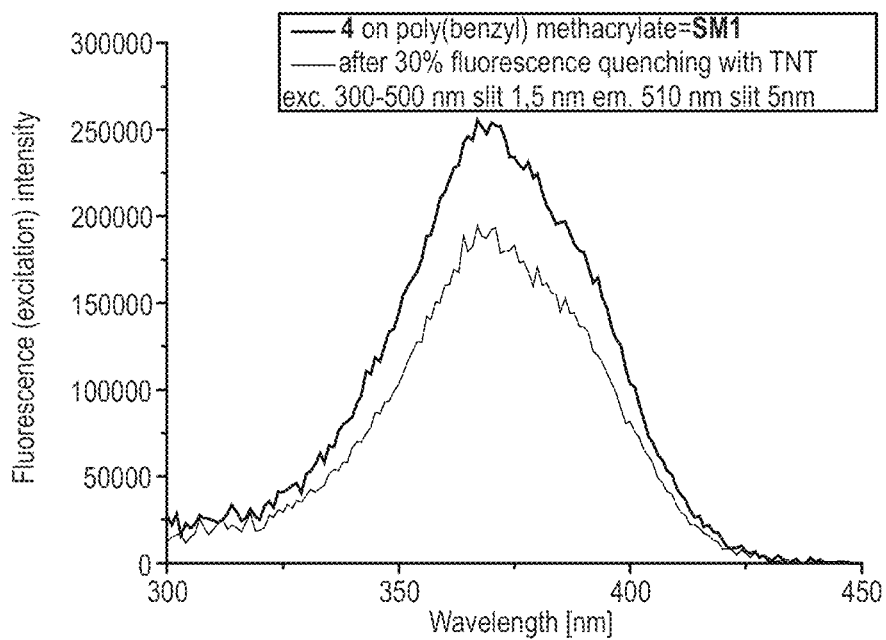
FIG. 12 shows the fluorescence excitation spectrum of detection reagent 4 on glass coated by poly(benzyl methacrylate) (SM1) before and after 30% quenching of the fluorescence by TNT in open air at room temperature.
Figure 13:
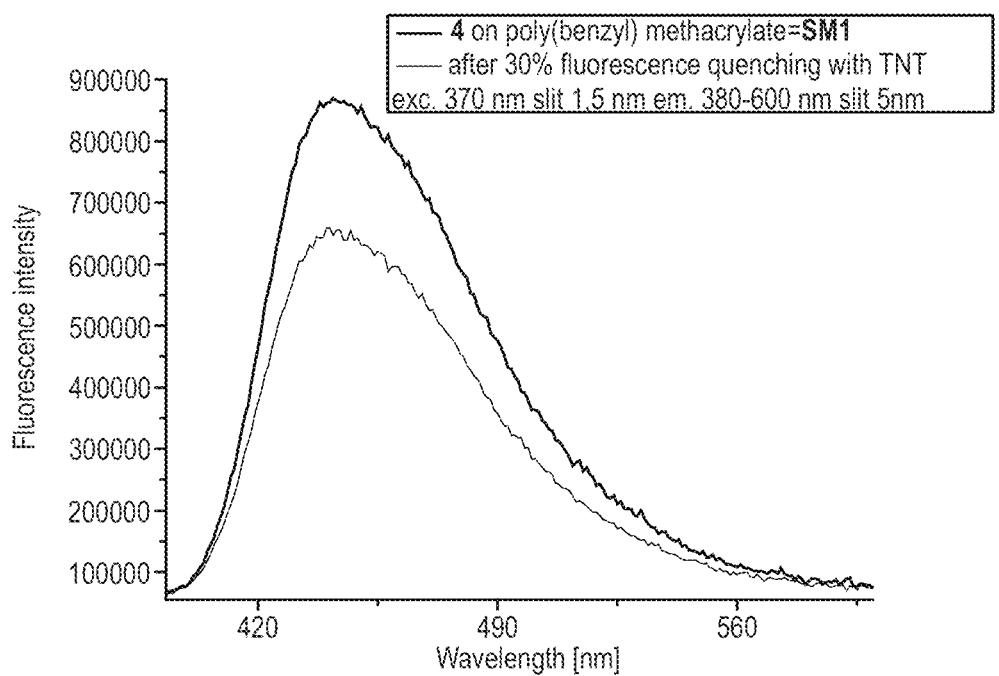
FIG. 13 shows the fluorescence spectrum of detection reagent 4 on glass coated by poly(benzyl methacrylate) (SM1) before and after 30% quenching of the fluorescence by TNT in open air at room temperature.
Figure 14:
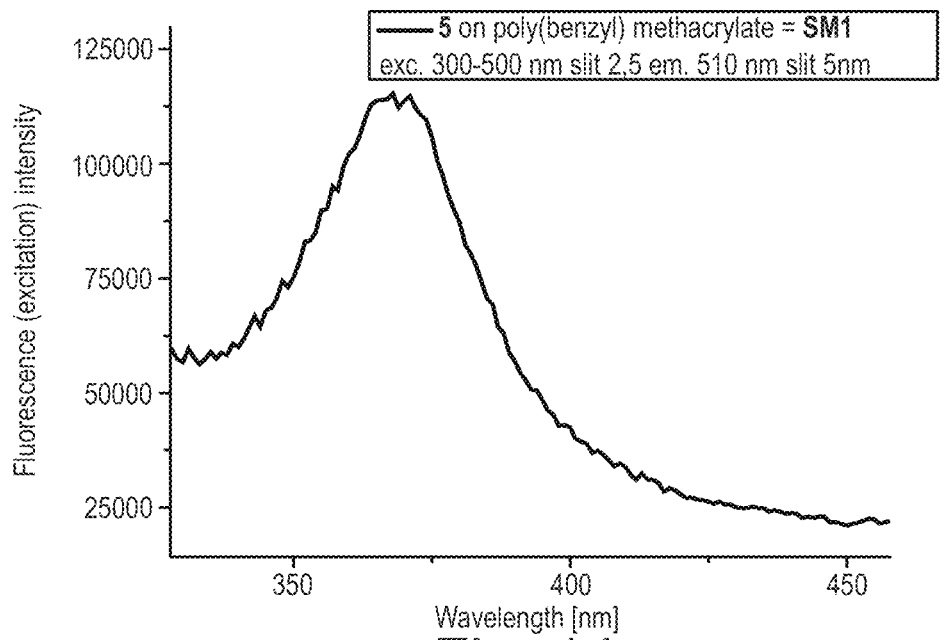
FIG. 14 shows the fluorescence spectrum of detection reagent 5 on glass coated by poly(benzyl methacrylate) (SM1).
Figure 15:
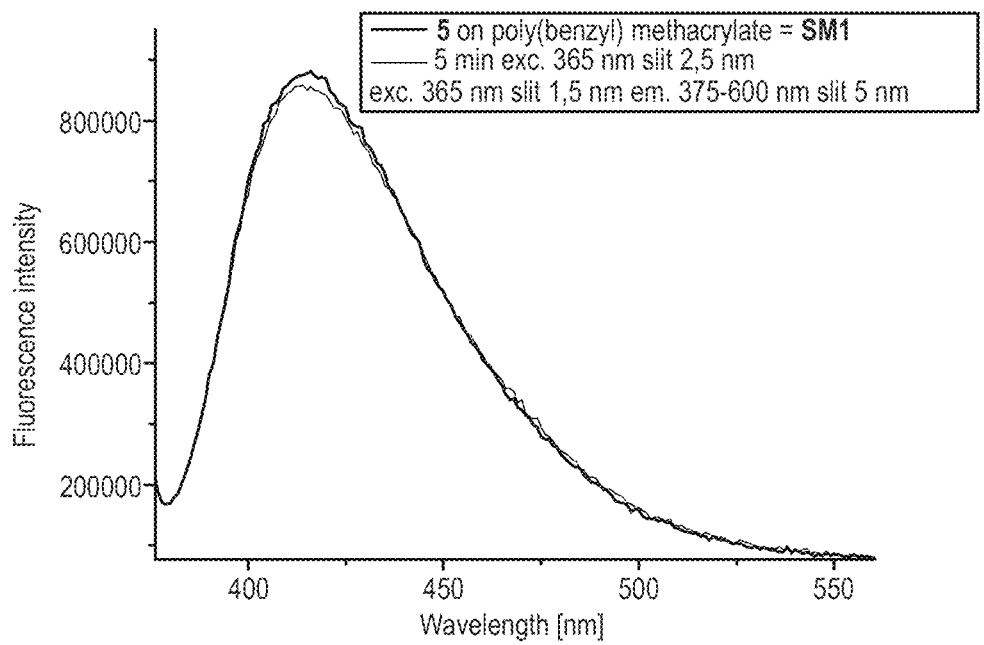
FIG. 15 shows the results or the fluorescence spectrum of tests on the photostability of detection reagent 5 on glass coated by poly(benzyl methacrylate) before and after continuous irradiation at higher excitation intensity.
Figure 16:
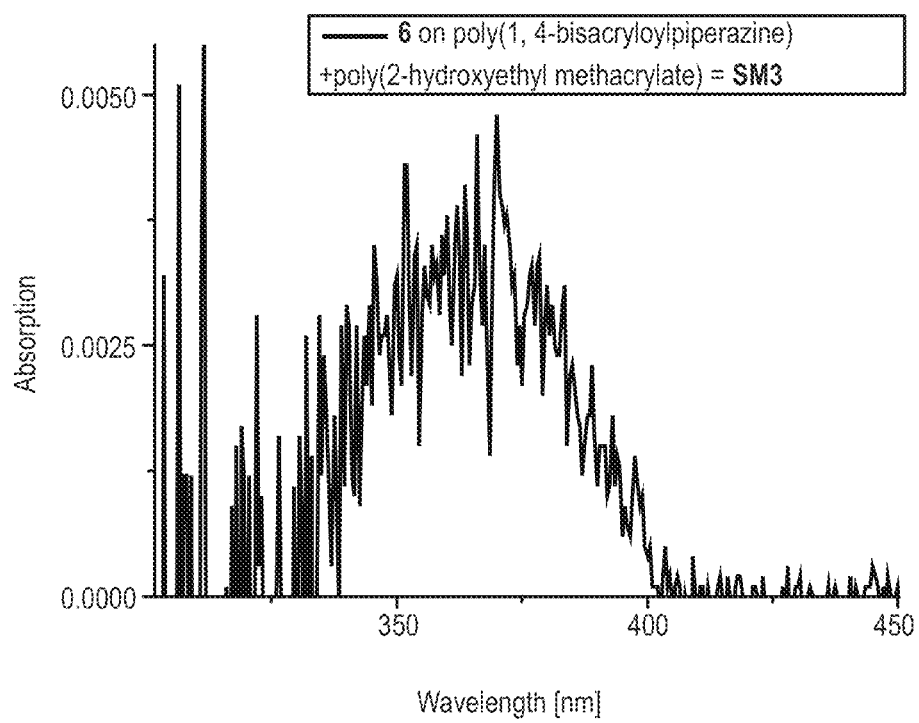
FIG. 16 shows the absorption spectrum of detection reagent 6 on glass polymerised with 1,4-bisacryloylpiperazine/2-hydroxyethyl methacrylate (SM3).
Figure 17:
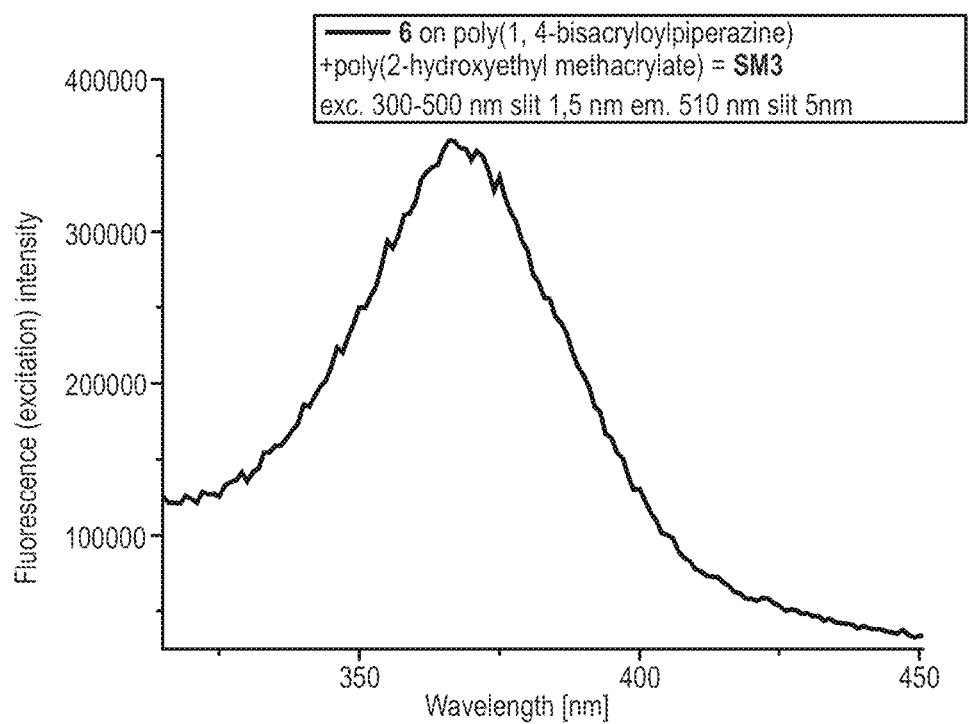
FIG. 17 shows the fluorescence excitation spectrum of detection reagent 6 on glass polymerised with 1,4-bisacryloylpiperazine/2-hydroxyethyl methacrylate (SM3).
Figure 18:
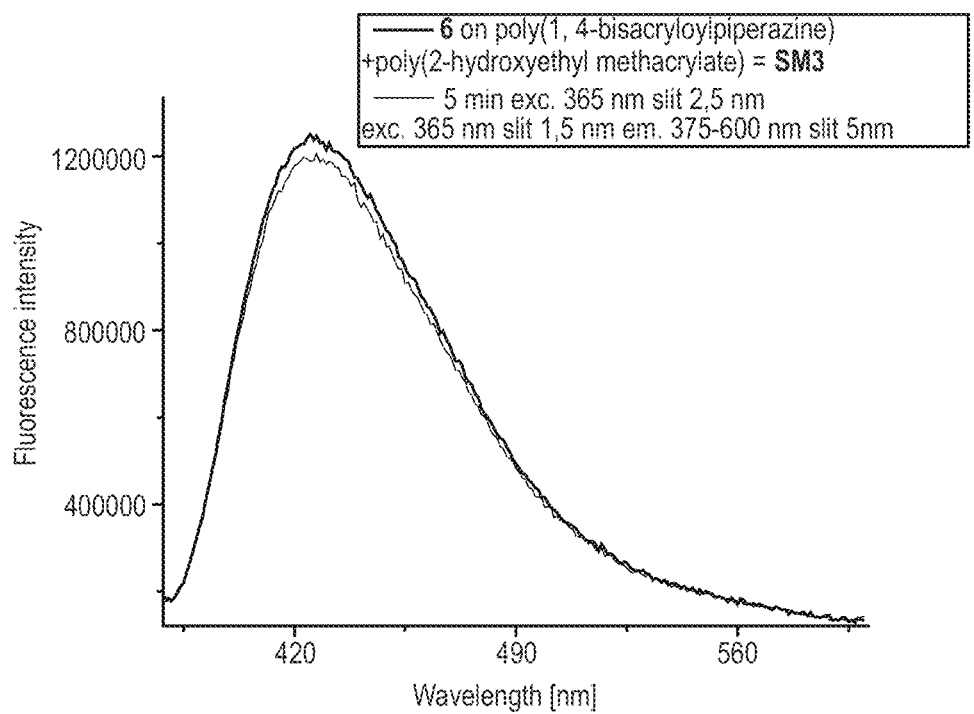
FIG. 18 shows results or the fluorescence spectrum of tests on the phoostability of detection reagent 6 on glass polymerised with 1,4-bisacryloylpiperazine/2-hydroxyethyl methacrylate (SM3) before and after continuous radiation at higher excitation intensity.
Figure 19:
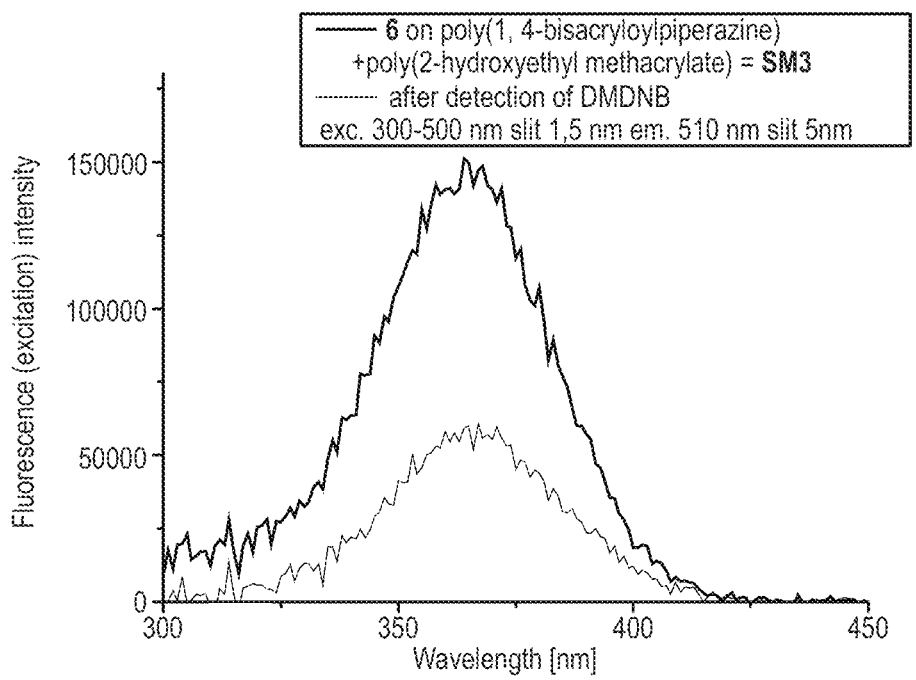
FIG. 19 shows the fluorescence excitation spectrum of detection reagent 6 on glass polymerised with 1,4-bisacryloylpiperazine/2-hydroxyethyl methacrylate (SM3) before and after >50% quenching of the fluorescence by DMDNB in open air at room temperature.
Figure 20:
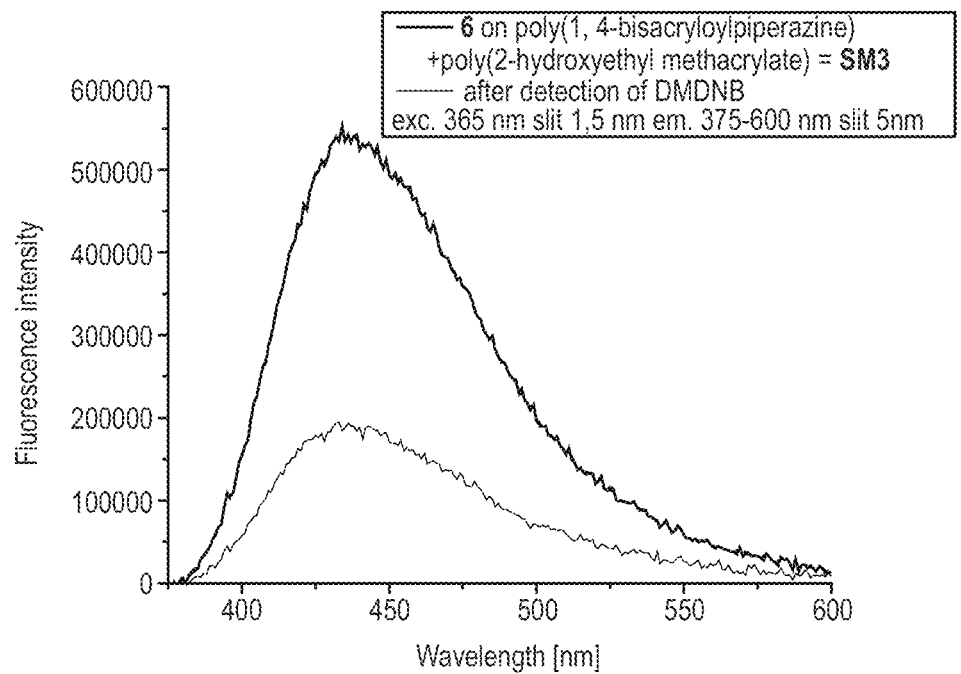
FIG. 20 shows the fluorescence spectrum of detection reagent 6 on glass polymerised with 1,4-bisacryloylpiperazine/2-hydroxyethyl methacrylate (SM3) before and after >50% quenching of the fluorescence by DMDNB in open air at room temperature.
Figure 21:
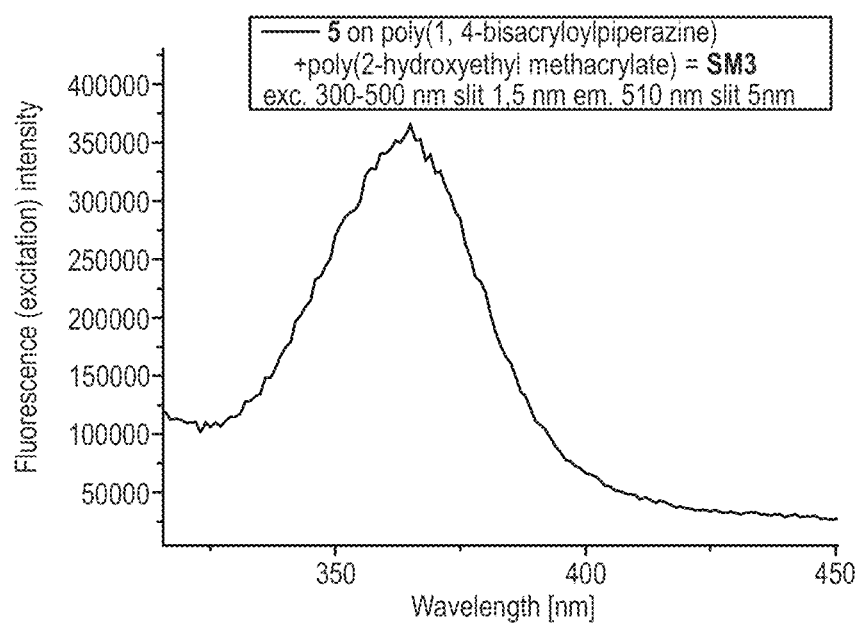
FIG. 21 shows the fluorescence excitation spectrum of detection reagent 5 on glass polymerised with 1,4-bisacryloylpiperazine/2-hydroxyethyl methacrylate (SM3)
Figure 22:
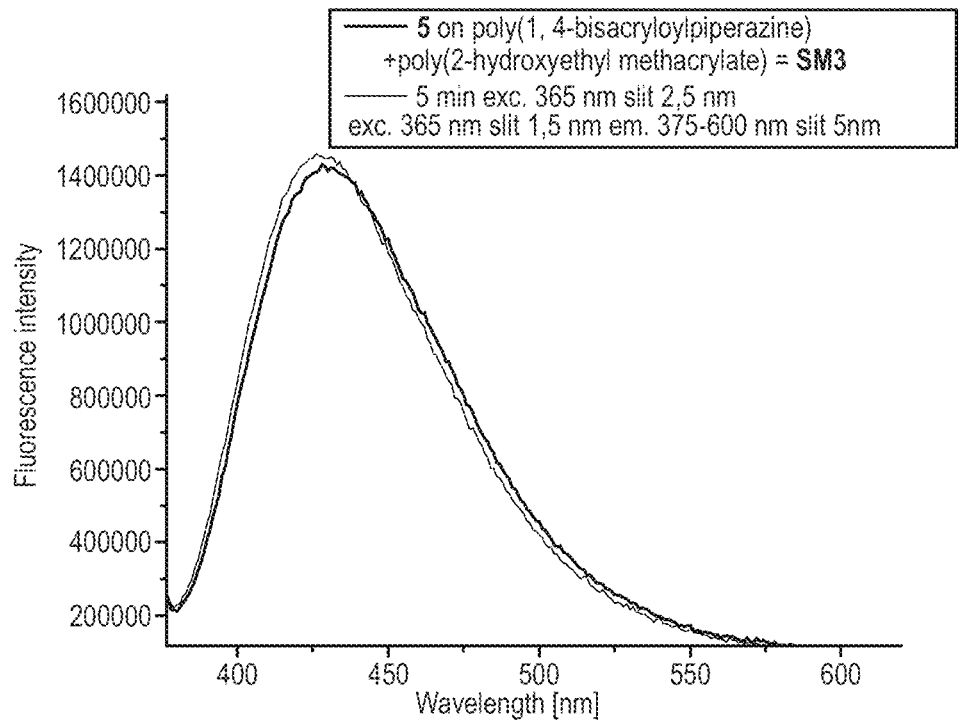
FIG. 22 shows the fluorescence spectrum of detection reagent 5 on glass polymerised with 1,4-bisacryloylpiperazine/2-hydroxyethyl methacrylate (SM3) before and after continuous radiation at higher excitation intensity.
Figure 23:
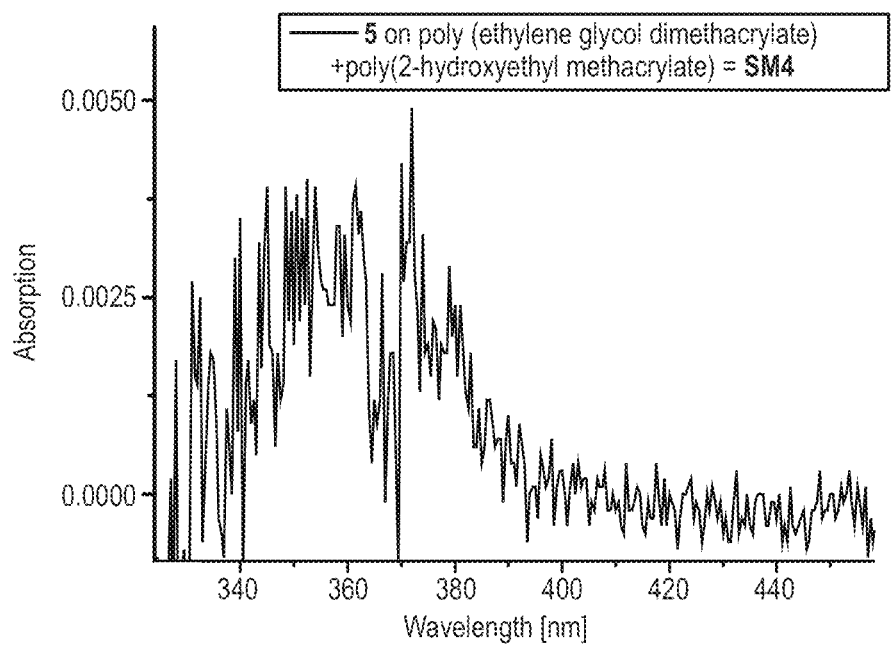
FIG. 23 shows the absorption spectrum of detection reagent 5 on glass polymerised with ethylene glycol dimethacrylate/2-hydroxyethyl methacrylate (SM4).
Figure 24:
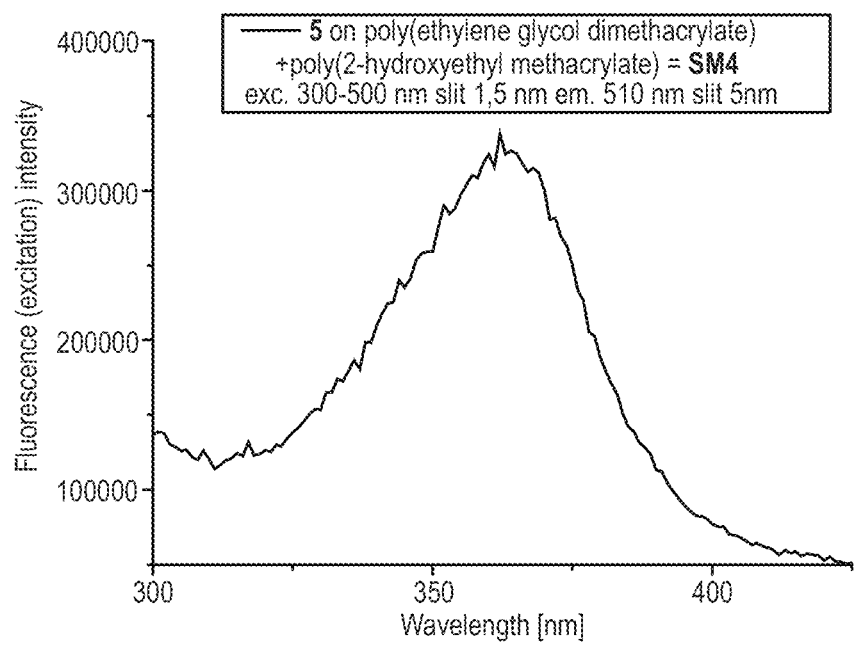
FIG. 24 shows the fluorescence excitation spectrum of detection reagent 5 on glass polymerised with ethylene glycol dimethacrylate/2-hydroxyethyl methacrylate (SM4).
Figure 25:
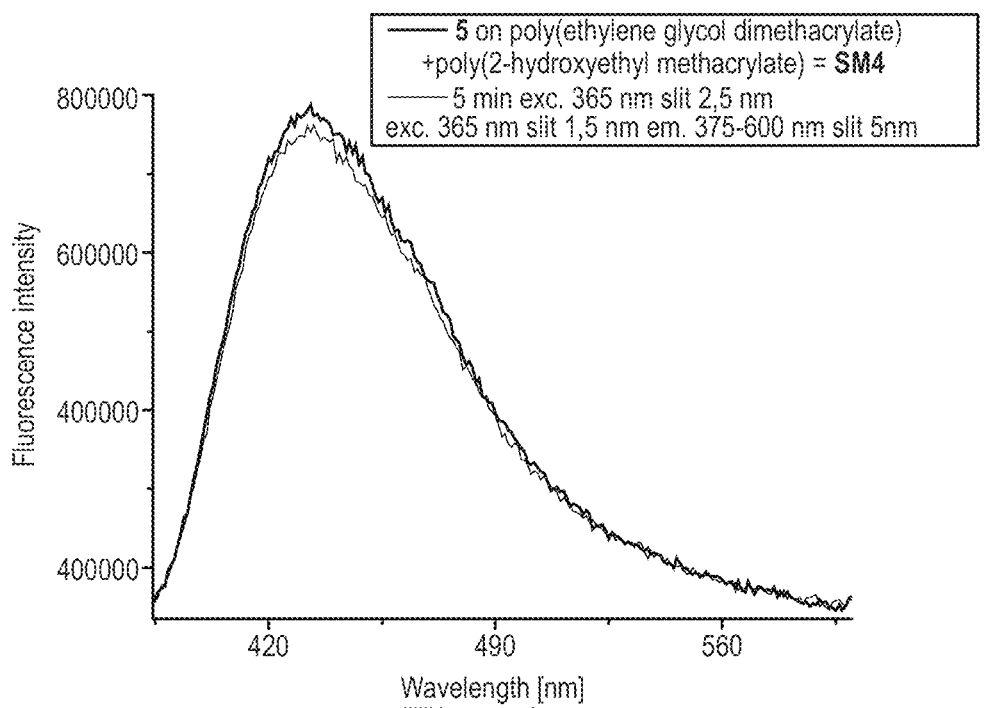
FIG. 25 shows the fluorescence spectrum of detection reagent 5 on glass polymerised with ethylene glycol dimethacrylate/2-hydroxyethyl methacrylate (SM4) before and after continuous irradiation at higher excitation intensity.

The proposed detection method is based on providing a detection reagent which is adsorbed to solid phase. The solid phase is preferably a homogeneous polymer film of constant thickness on a glass substrate. The polymer film is coated with a fluorescent, molecular probe, which is used under the measurement conditions as a specific detection reagent for NOx explosives and marker substances (for example for TNT and DMDNB) that are of practical relevance. The fluorescence probe comprises a triphenylamine core and an electron-withdrawing phenyl unit covalently bonded to the core in the para position by means of a triple bond. A fluorescence probe in this context is understood to mean a molecule that indicates the presence of an explosive by specific fluorescence properties, thus in the present case a triphenylamine derivative, which is present in a dye-polymer composition adapted specifically for the complexing of the corresponding explosive.

A receptor unit is understood in this context to mean a motif that interacts specifically with the NOx explosive to be detected, comprising a phenylamino derivative, which is capable of forming radical cations by releasing an electron to the acceptor (NOx explosive). The receptor unit, comprising the phenylamino group is selected such that it can stabilise the radical cation. The two unsubstituted phenyl groups of the phenylamino group allow sterically a quick interaction with the explosive and at the same time increase the fluorescence quantum yield of the molecular probe.

The receptor unit of the molecular probe is also adapted such that on the one hand it gives up an electron to the explosive as donor and on the other hand withdraws this again depending on the volatility of the explosive or dwell time thereof on the sensor surface. The bonding that has occurred of the explosive to the receptor unit is thus detected with high sensitivity on the basis of a change to the fluorescence optical, in particular fluorescence spectroscopy characteristics of the fluorescence probe, wherein the position of the absorption maximum of the fluorescence probe bonded in said portion typically has not changed significantly for an excitation radiation. This facilitates the reading of the measurement values with a portable reader ("hand-held device") that operates at a fixed excitation wavelength (for example an LED) and that is usually inexpensive and robust.

An amount of the NOx compound bound by the probe per unit of time (at given temperature) preferably corresponds to a defined concentration of the explosive in the air or as a water sample or wipe sample with initially unknown concentration of the explosive of a defined sample mass with an initially unknown content of the explosive. Naturally, the temperature has a certain influence on the establishment of equilibrium at molecular level. Any interfering influences, such as the temperature-dependent regeneration of the sensor layers can be adapted to the measurement conditions by means of a suitable calibration. The fluorescence probes can thus be used without difficulty for the proposed detection of explosives in a temperature range of 0-130° C.

The proposed fluorescent probes SM1 and SM2 are particularly suitable for the detection of the following explosives and markers: TNT, DNT, tetryl, PETN, NG, EGDN, RDX, HMX and $NH_4NO_3$.

The proposed fluorescence probe SM3 is particularly suitable for the detection of the following explosives and marker substances: DNT, DMDNB, PETN, NG, $NH_4NO_3$ and EGDN.

The proposed fluorescence probe SM4 is particularly suitable for the detection of the following explosives and markers: TNT, DNT, DMDNB, PETN, NG, $NH_4NO_3$ and EGDN.

Accordingly, a detection method for the quantitative and qualitative detection of these explosives in the air, as wipe samples from surfaces, and in water samples is proposed. The detection method is characterised in particular in that it can also be performed without difficulty by an individual who is not specially trained; costly and laboratory-bound measurement techniques can be spared.

As shown on the basis of the example of compounds 4, 5 and 6, the air stability and the sensitivity of the indicators can be modified by the polymer material, and for example the selectivity of the NOx explosive to be detected can be increased. In the case of volatile nitro compounds, such as the marker DMDNB, the only consequence is that it is not enriched on a thin polymer surface, such as poly(benzyl methacrylate), because the pores required for this are absent. The dwell time of DMDND on this polymer film is therefore very short, which explains the low fluorescence quenching and thus the weak interaction with the molecular probes.

The composition of the polymer material for detection of non-volatile explosives, such as TNT and RDX, appears to be of secondary importance. The layer thickness of the polymer film or the layer thickness of the molecular probe(s) is better suited to control the sensitivity of an analyte-sensitive layer. According to the present understanding, an increased selectivity is achieved by the reduction of the concentration of the indicator and by a higher temperature on the sensor film. Results are summarised in Table 4 below.

TABLE 4

| Measurement head temp. [° C.] | Conc. [µM] | TNT (5%) [sec.] | MA (5%) [sec.] | TNT (10%) [sec.] | MA (10%) [sec.] |
|---|---|---|---|---|---|
| 115 | 556 | 41 | 61 | 63 | 123 |
| 115 | 278 | 59 | 101 | 91 | e. |
| 115 | 222 | 55 | 201 | 85 | e. |
| 115 | 111 | 68 | n.e. | 102 | n.e. |
| 115 | 56 | 91 | n.e. | n.e. | n.e. |
| 150 | 556 | 29 | 52 | 42 | 159 |
| 150 | 278 | 29 | 91 | 52 | e. |
| 150 | 222 | 31 | 74 | 47 | 269 |
| 150 | 111 | 46 | 185 | 78 | e. |
| 150 | 56 | 71 | e. | n.e. | n.e. |

Explanations:
Measurement head temp.=Measurement head temperature or the temperature at the air sample inlet on the hand-held device. The air sample inlet or outlet of the used hand-held device is funnel-shaped and can be heated to a temperature that can be adjusted electively. The temperature typically used here of the measurement head was 150° C. This enables the resublimation of non-volatile sample material on the analyte-sensitive layer.

Conc. [µM]=Concentration of detection reagent 4 in 2-propanol, applied in each case by means of spin coating to the particular polymer.

TNT (5%)=Fluorescence quenching of the starting signal by 5% during the measurement of a TNT specimen at room temperature with a concentration in air in the ppb range.

MA (5%)=Fluorescence quenching of the starting signal by 5% during the measurement of a musk ambrette specimen at room temperature with a concentration in air in the ppb range.

TNT (10%)=Fluorescence quenching of the starting signal by 10% during the measurement of a TNT specimen at room temperature with a concentration in air in the ppb range.

MA (10%)=Fluorescence quenching of the starting signal by 10% during the measurement of a musk ambrette specimen at room temperature with a concentration in air in the ppb range.

e.=the detection limit of 5% or 10% was reached after 5 minutes.

n.e.=the detection limit of 5% or 10% was not reached even after 5 minutes.

The dwell time of the explosives on the analyte-sensitive layer can also be controlled by means of the temperature of the sensor material adjustable by heating. Under the conditions optimised for the measuring apparatus used, TNT can continuously quench the fluorescence of the analyte-sensitive layer, whereas structurally related mask compounds on the same analyte-sensitive layers (SM1 and SM2) achieve a quick adsorption-desorption equilibrium and therefore did not reach the target value for the fluorescence quenching. The detection reagents proposed here, by virtue of the absence of sterically demanding groups (for example tert-butyl groups), advantageously have a molecular configuration that allows facilitated interaction with the analyte. In the case of conjugated polymers, the incorporation of sterically demanding groups is necessary in order to prevent the self-quenching of the fluorescence by aggregate formation. In the case of the sensor materials SM1-SM4, the non-fluorescent polymer performs this task. The incorporation of sterically demanding groups in the dye structure of detection reagents 4-6 is therefore not necessary. Sterically demanding groups of this kind have only a small influence on the selectivity of the sensor materials, and therefore the proposed use of the polymer film drastically reduces the costs for obtaining an analyte-sensitive layer, for example by virtue of reduced synthesis effort. Further advantages of the sensor materials SM1-SM4 compared to the AFPs are given from the fact that the properties of the sensor materials can be adapted to the analyte properties in order to increase the efficiency thereof by simple modification of the molecular structure of the detection reagents, by production of copolymers or reagents or catalysts adsorptively bonded to the polymer, and by different layer thicknesses (1-2000 nm).

As can be seen, the detection method supported on the relatively hydrophobic fluorescence indicators 4, 5 and 6 is based on a receptor unit, acting as electron donor, of the detection reagents for the explosive in question in the form of a triphenylamine motif, which can stabilise (radical) cations formed in the dye molecule and thus promotes fluorescence quenching.

Various methods can be used in order to apply the probes to the homogeneous surface of the corresponding polymer material. For example, the corresponding amounts of the dissolved substances in a suitable solvent mixture can be applied to the carrier by means of a spin coater, spray coater, piezoelectric metering system, a nanoplotter or using an adapted inkjet printer. Commercially available single-drop metering systems also provide reproducible results. Similarly, the dyes can also be applied by a suitable stamping technique or contact printing method.

The carrier material in contact with the air containing the explosive to be detected advantageously does not enter into any disadvantageous interaction with the explosive, that is to say is inert.

The inert carrier material is preferably colourless, transparent polymer on a solid substrate, for example colourless glass, such that excitation light (360-370 nm) is not absorbed. The form of the ready-to-use carrier material can be freely selected, but its form and size are preferably adapted to a holding device, and this is adapted to the used reader. The size is advantageously selected such that the air flow contaminated with the NOx compounds detects the entire sensor layer.

In accordance with practical embodiments, cover slips used typically in microscopy are used as inert carrier material. For example, commercially available round cover slips with a diameter of 3-20 nm can be used as inert substrate. The surface of the substrate is preferably flat. However, the substrate can have a curved surface at least in portions and can surround a cavity which has at least one inlet opening for the supply of the analyte and at least one outlet opening for the discharge of the analyte. A polymer film is advantageously formed on the inner surface or a cavity portion. Different polymer layers can also be arranged adjacently to one another in part, so that the substrate is divided into a number of zones. In accordance with a further embodiment, an otherwise homogeneous polymer layer can be divided into a number of zones on the substrate (flat or cavity inner face) by applying different detection reagents adjacently to one another on the carrier. Sensitive layers having different properties are thus formed on a one-piece substrate. The arrangement of said layers can be selected advantageously such that the flow of the medium to be analysed (analyte, or air which only potentially contains the analyte) passes over or through these zones as a result of the geometric arrangement of said layers in a specific order and/or with a certain flow rate and/or at a specific pressure. The dwell time of the analyte can advantageously thus be varied within wide limits in order to ensure reliable detection.

Figure 30:
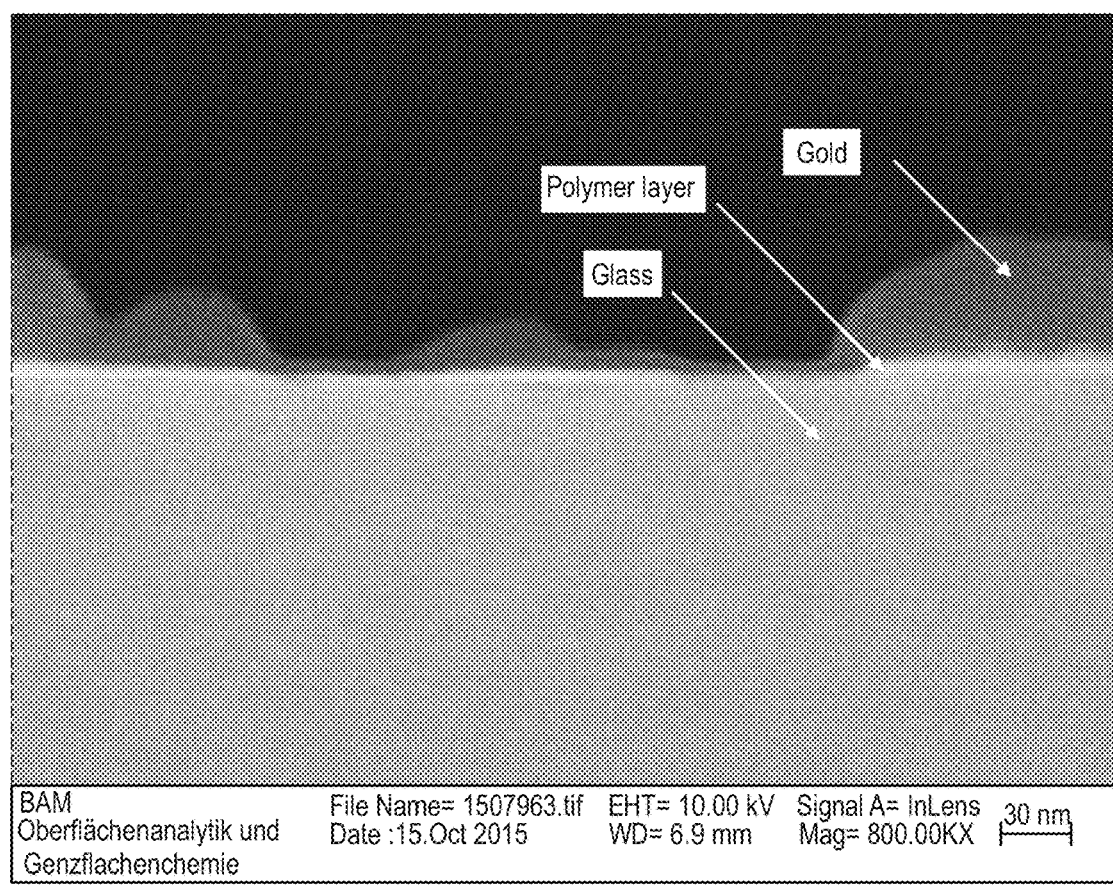
FIG. 30 shows the cross-sectional image of a sensor material vapour-coated with gold SM1 under a scanning electron microscope. In the image, the structure of the broken carrier substrate (glass) (bottom) with the polymer film arranged thereon (middle) and the gold layer (top) can be seen. The layer thickness of the polymer film is <5 nm.
Figure 31:
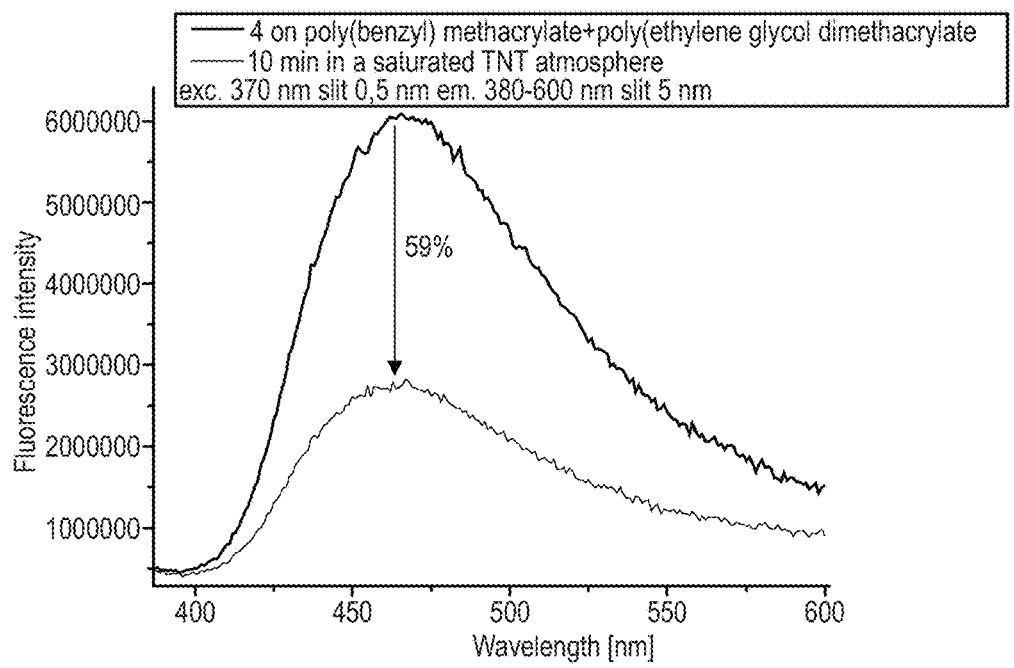
FIG. 31 shows, in the fluorescence spectrum, the reduction of the fluorescence intensity of the fluorescence probe 4 on an apolar polymer film, produced starting from benzyl methacrylate (BMA) and ethylene glycol dimethacrylate (EDMA) before and after 59% quenching of the fluorescence by a TNT-saturated air atmosphere at room temperature within 10 minutes. Excitation was achieved by means of UV (370 nm), the emission signal was detected in the wavelength range 380-600 nm.
Figure 32:
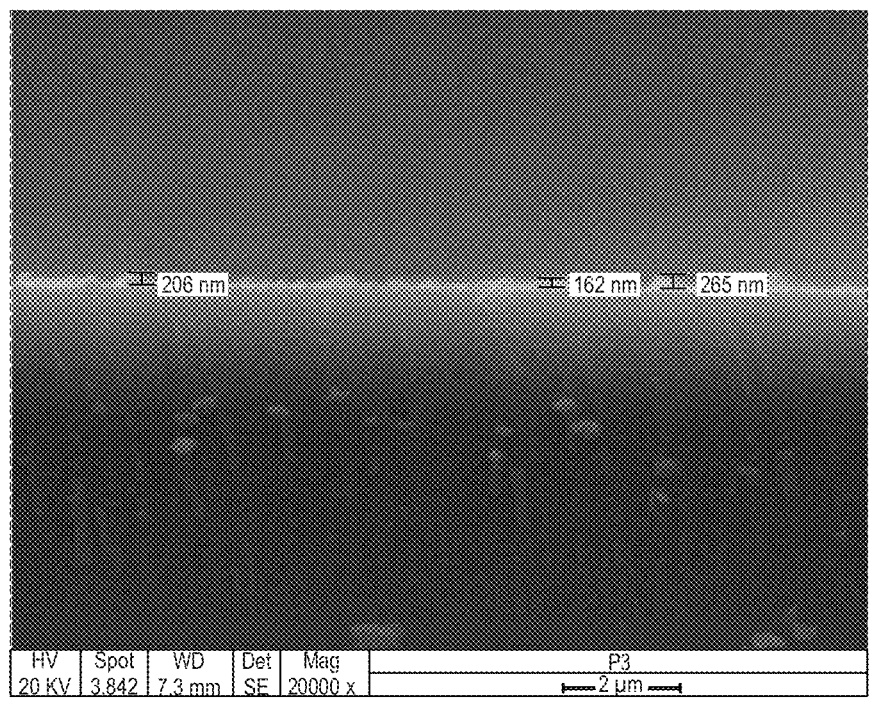
FIG. 32 shows the cross-sectional image of the polymer film coated with detection reagent 4 produced from benzyl methacrylate (BMA) and ethylene glycol dimethacrylate (EDMA) under a scanning electron microscope. In the image, the structure of the broken carrier substrate (glass) (bottom) with the polymer film particles arranged thereon with a diameter of 160-265 nm can be seen. As the glass substrate with the analyte-sensitive layer was broken, polymer particles passed from the analyte-sensitive layer to the surface of the break of the glass substrate.
Figure 33:
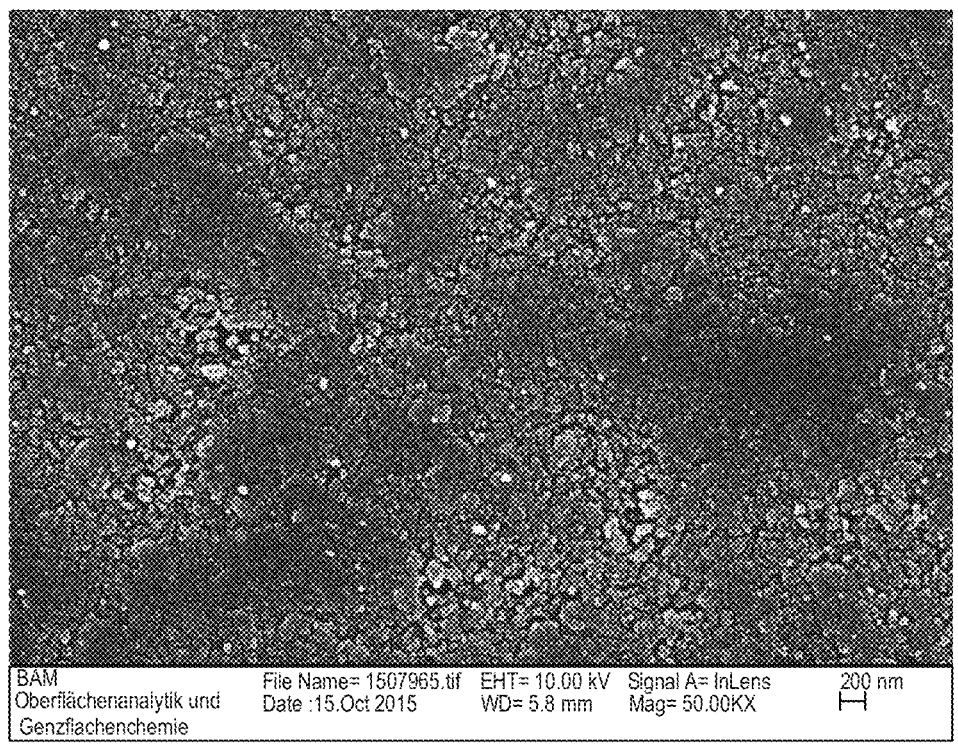
FIG. 33 shows the surface of a sensor material SM3 vapour-coated with gold under scanning electron microscope. In the image, the structure of the pores can be seen, which allow the diffusion of the analyte into the polymer.
Figure 34:
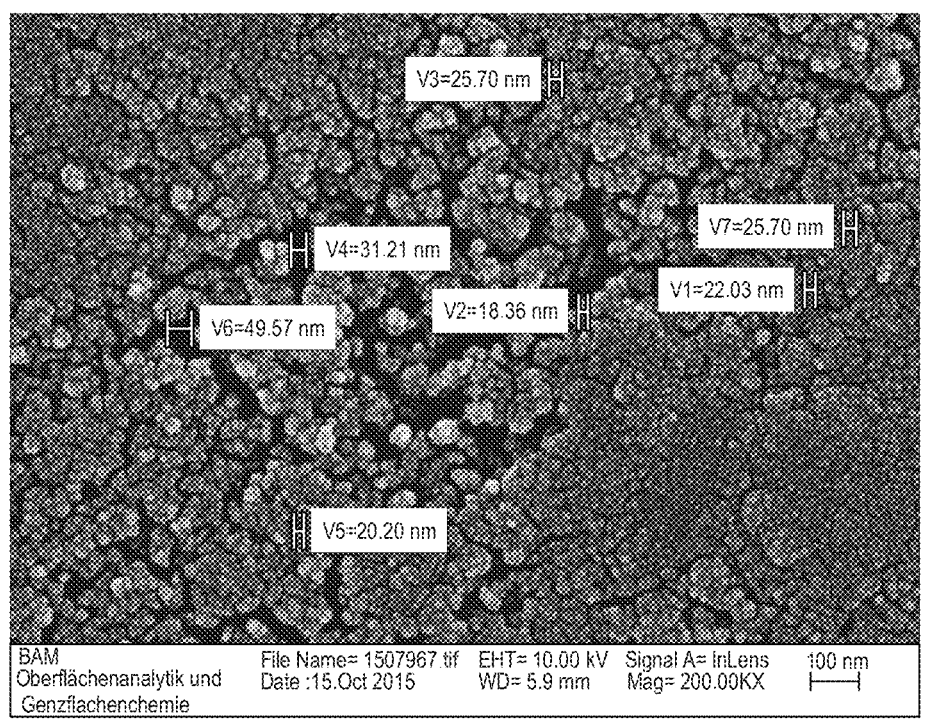
FIG. 34 shows the surface of a sensor material SM3 vapour-coated with gold under scanning electron microscope, or the enlargement of the image in FIG. 33. In the image, the polymer particles and the structure of the pores can be seen. The diameter of the polymer particles is 18-25 nm. The pore size is 30-50 nm.
Figure 35:
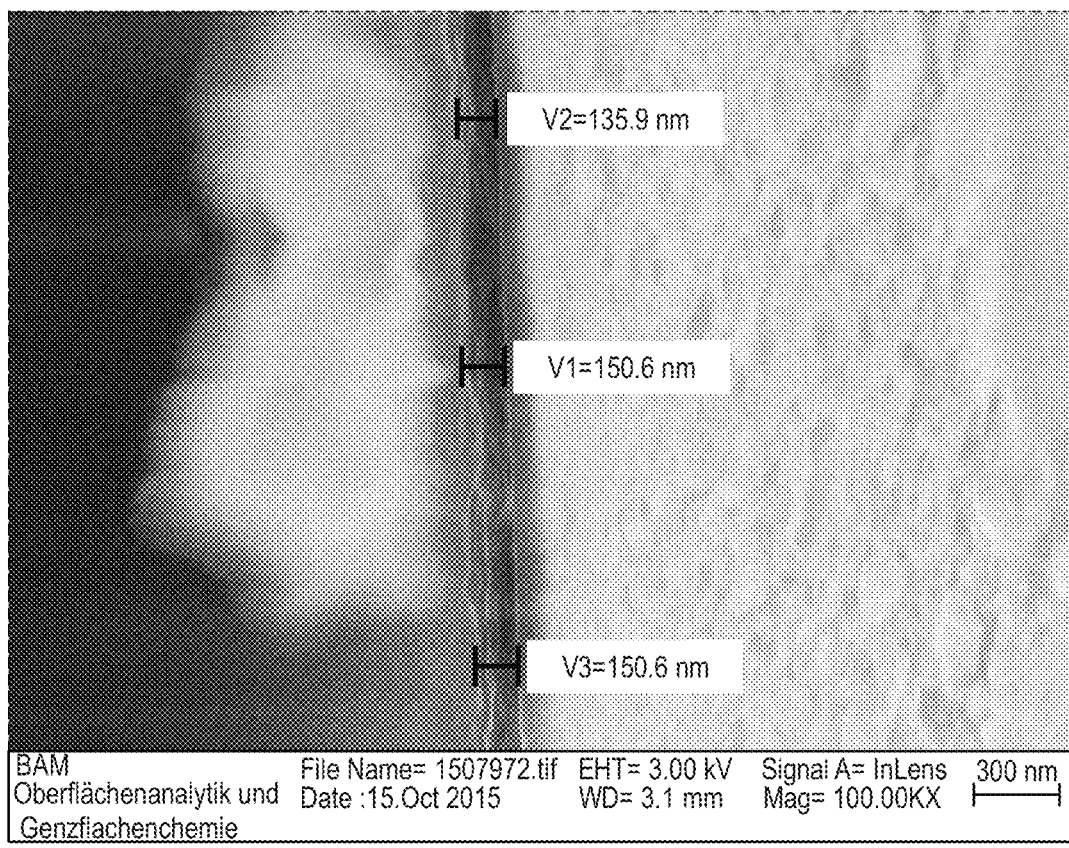
FIG. 35 shows the cross-sectional image of a sensor material vapour-coated with gold SM3 under scanning electron microscope. In the image, the structure of the broken carrier substrate (glass) (right) with the polymer film arranged thereon can be seen. The layer thickness of the polymer film is 135-150 nm.
Figure 36:
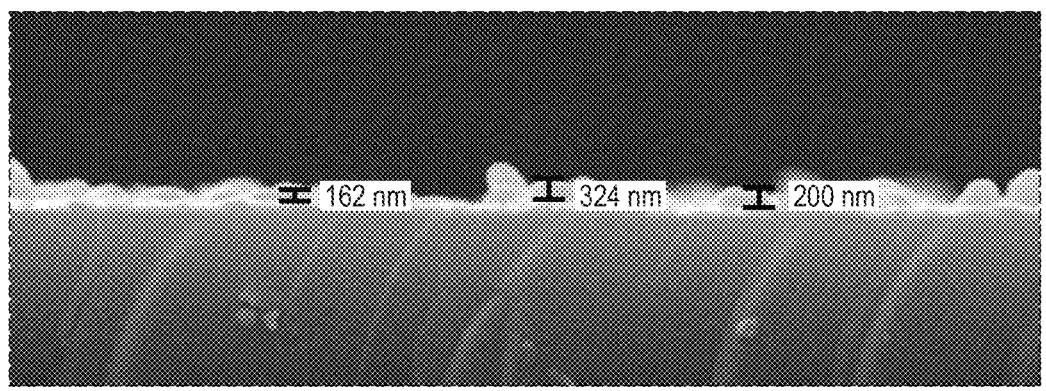
FIG. 36 shows the cross-sectional image of a sensor material vapour-coated with gold SM4 under scanning electron microscope. In the image, the structure of the broken carrier substrate (glass) (bottom) with the polymer film arranged thereon can be seen. The layer thickness of the polymer film is 160-325 nm.
Figure 37:
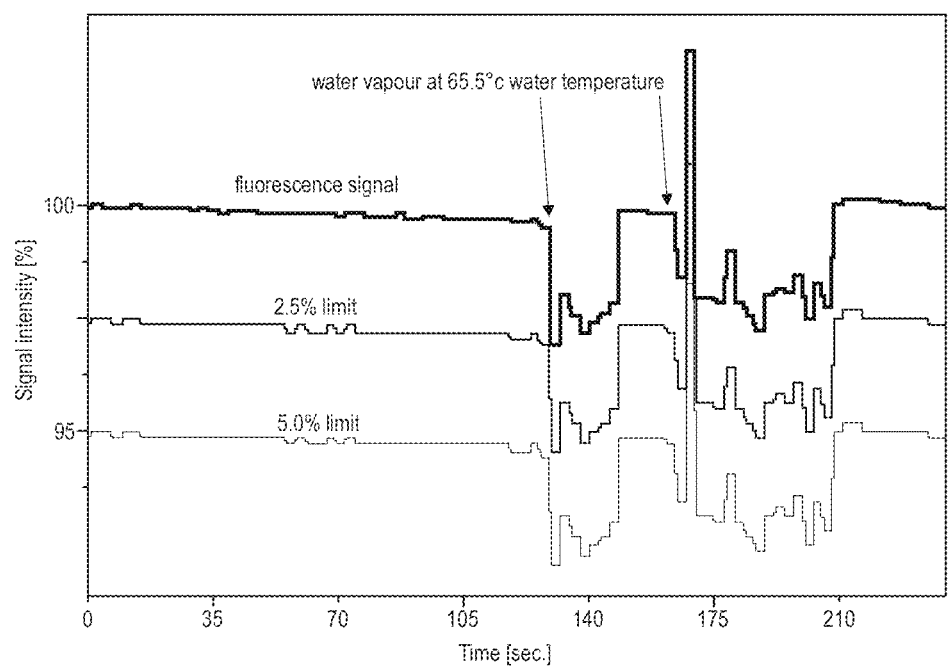
FIG. 37 shows the quenching of the fluorescence of the sensor material SM1 in the handheld device, with two measurements of water vapour 1 cm above the water surface at a water temperature of 65.5° C. and a measurement head temperature of 120° C., by 2.7% at most. Red marks the 2.5% limit (middle line) and blue marks the 5% limit (lower line); these are not reached.

The layer thickness of the carrier material, i.e. the layer thickness of the polymer layer arranged on the inert substrate, can be used to control a measurement sensitivity of the detection method. By use of cross-linking agents, the layer thickness can be increased from 1 to 5 nm (FIGS. 30) to >1 to 2 μm.

In accordance with an exemplary embodiment, an analyte-sensitive layer can comprise individual polymer chains covalently bonded to the substrate and in the form of a polymer carpet (brushes), wherein the covalently bonded polymer chains comprise on average from 18 to 26, typically from 20 to 24, preferably 22 ±1 benzyl methacrylate units.

Figure 26:
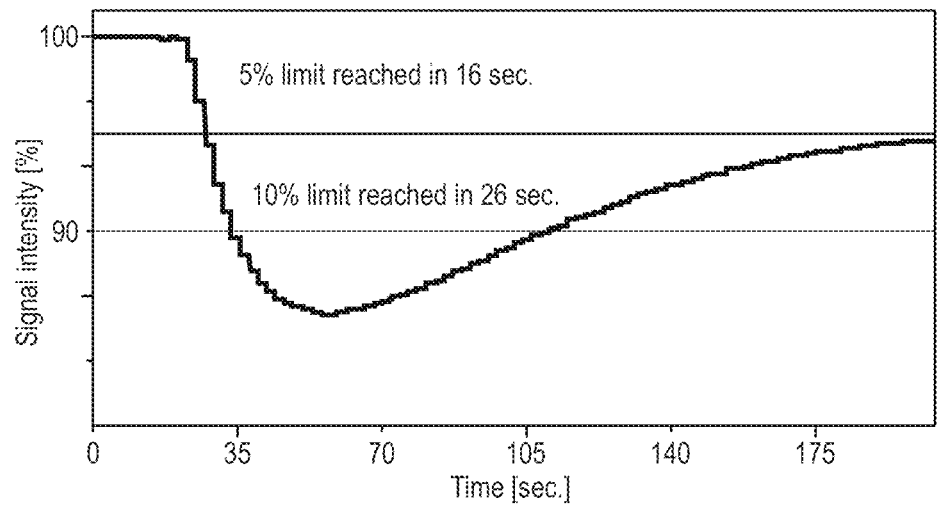
FIG. 26 shows the quenching (left) with 1.9 ng TNT wipe sample, which is heated at the measurement head of the hand-held device to 150° C., and the increase in the fluorescence signal (upper line) of the sensor material SM1 upon regeneration (right), measured in the hand-held device. Red marks the 5% limit (middle line), which is reached in 16 seconds, and blue marks the 10% limit (lower line) of a 10% fluorescence quenching, which is reached in 26 seconds.
Figure 27:
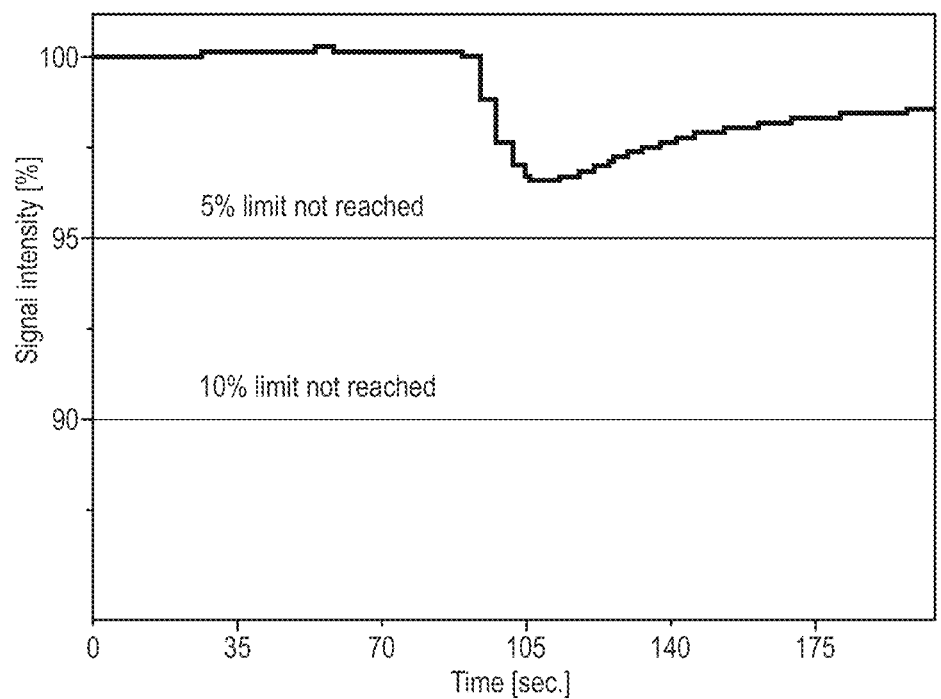
FIG. 27 shows the quenching (left) with 2.2 ng musk ambrette wipe sample, which is heated at the measurement head of the hand-held device to 150° C., and the increase in the fluorescence signal (upper line) of the sensor material SM1 upon regeneration (right), measured in the hand-held device. Red marks the 5% limit (middle line), and blue marks the 10% limit (lower line); these are not reached.
Figure 28:
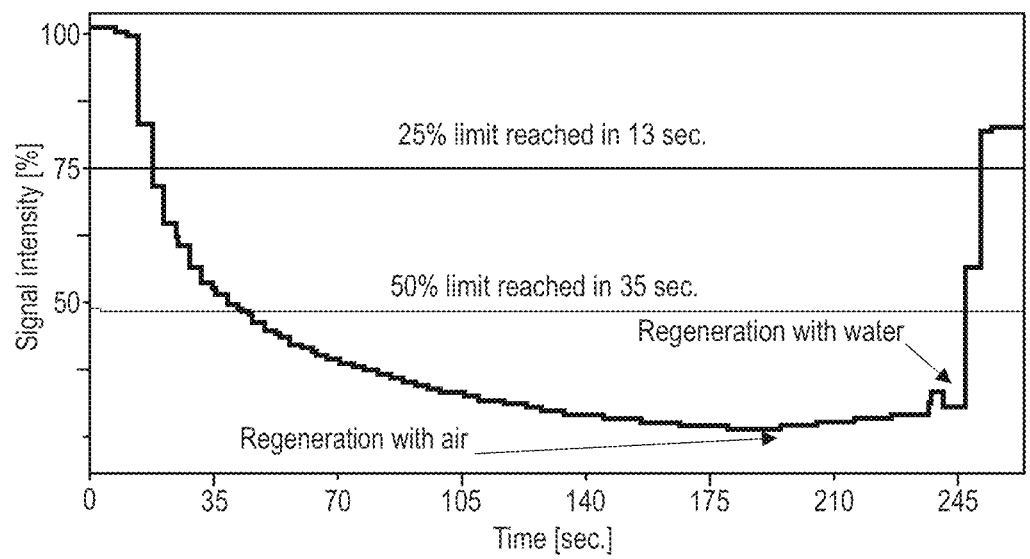
FIG. 28 shows the quenching (left) with DMDNB at room temperature in open air and the increase in the fluorescence signal (upper line) of the sensor material SM3 upon regeneration (right) with water vapour, which was formed by vaporisation of 2 μL water at the measurement head heated to 120-150° C., measured in the hand-held device. Red marks the 25% limit (middle line), which is reached in 13 seconds, and blue marks the 50% limit (lower line) of a 50% fluorescence quenching, which is reached in 35 seconds.
Figure 29:
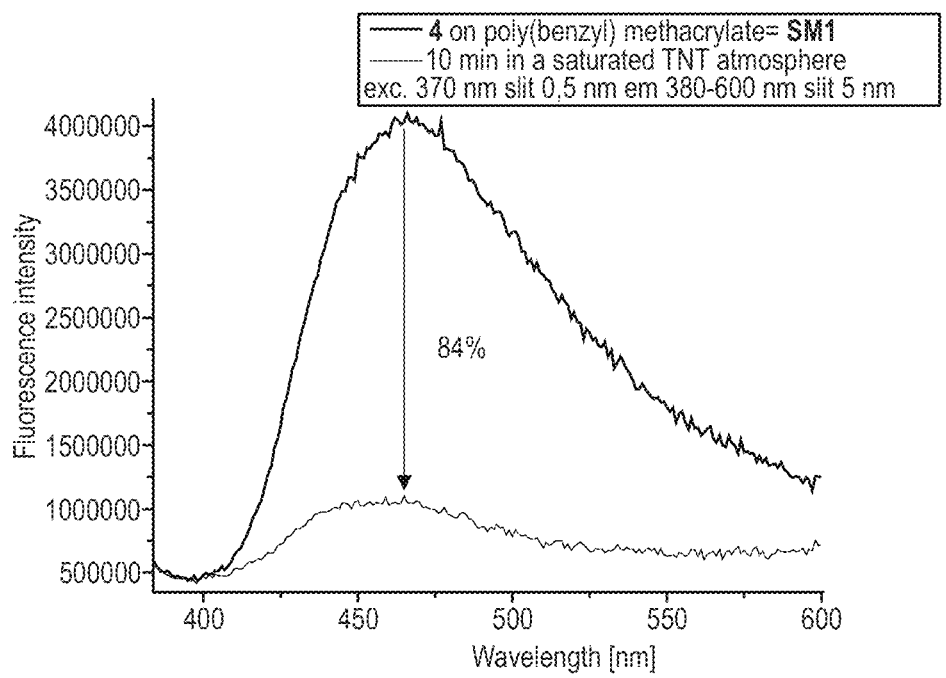
FIG. 29 shows, in the fluorescence spectrum, the reduction of the fluorescence intensity of the sensor material SM1, comprising the fluorescence probe 4 on an apolar polymer film, produced starting from benzyl methacrylate (BMA) before and after 84% quenching of the fluorescence by a TNT-saturated air atmosphere at room temperature within 10 minutes. Excitation was achieved by means of UV (370 nm), the emission signal was detected in the wavelength range 380-600 nm.

In order to examine the selectivity of the sensor materials SM1-SM4 for TNT, DNT, tetryl, PETN, NG, EGDN, RDX, HMX, $NH_4NO_3$ and DMDNB, measurements were taken of the solutions of the explosives and of some structurally related musk compounds using a mobile measuring apparatus (referred to here as a "hand-held unit"). In particular, SM1 and SM2 with TNT and SM3 with DMDNB demonstrated fluorescence quenching (FIGS. 26 and 28). When examining the cross-sensitivity for musk ambrette, which is not classed as an explosive or marker substance, but demonstrates interactions with the analyte-sensitive layer comparable to TNT, the detection limit for explosives was not exceeded.

It is known that molecular probes alone cannot differ between the examined explosives and materials that also have fluorescence-quenching properties. However, the likelihood of finding substances of this kind in the environment is typically very low. Exceptions are the numerous mask compounds, which can occur as constituents of various perfumes, cosmetic products and pesticides, in groundwater. The probe can therefore be used effectively for the selective detection of explosives based on NOx, depending on the polymer material, polymer layer thickness, dye layer thickness, measurement mode (wipe sample, water sample or air), signal pattern of the fluorescence quenching (or fluorescence intensification) and the signature of the regeneration phase. Furthermore, it is of course possible to take measurements of a sample using at least two probes, so as to be able to more accurately determine the composition of the sample.

Figure 38:
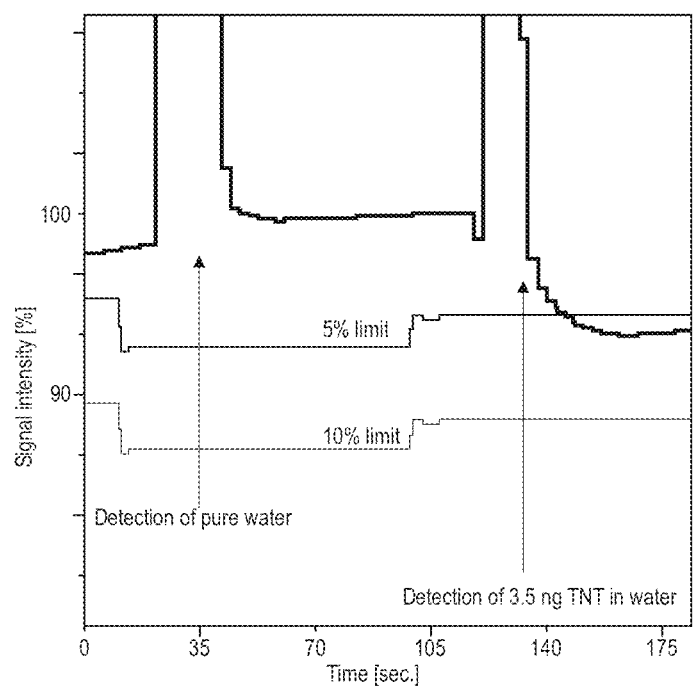
FIG. 38 shows the signal of the sensor material SM1 in the hand-held device before and after the measurement of 3 μL aqueous samples without and with TNT (1.18 mg/L, c=5.2 μM), which are vaporised on the measurement head of the hand-held device heated to 150° C. With the measurement of pure water, a fluorescence intensification was observed, which reverted back to the starting state. In the case of samples contaminated with TNT, a fluorescence intensification was likewise firstly observed, however as the signal increased it dropped back to the 5% TNT detection limit once the starting state had been reached and reached this detection limit in 39 seconds.
Figure 39:
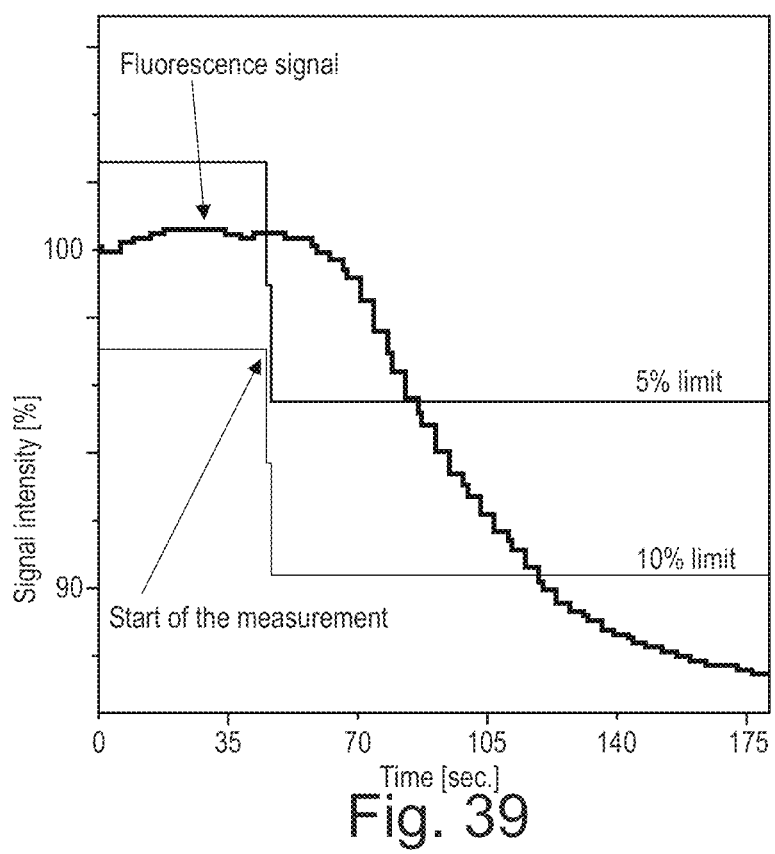
FIG. 39 shows the fluorescence signal of the sensor material SM1 in the hand-held device before and after the measurement over an aqueous TNT sample (1.18 mg/L, c=5.2 μM). The fluorescence quenching caused by TNT reaches the 5% TNT detection limit in 32 seconds in this case, and reaches the 10% TNT detection limit in 58 seconds.
Figure 40:
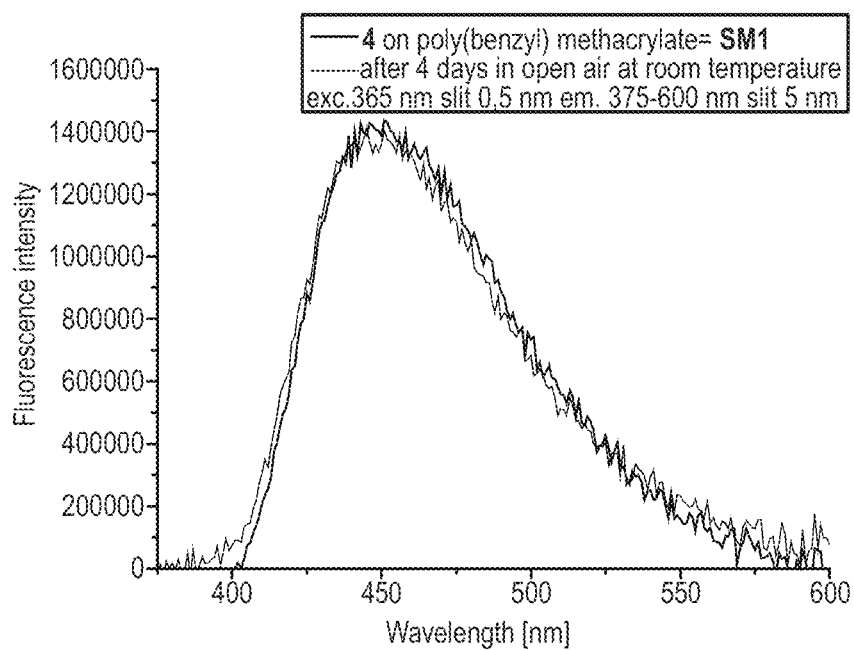
FIG. 40 shows results or the fluorescence spectrum of tests on the air stability of detection reagent 4 on glass coated by poly(benzyl methacrylate) (SM1) before and after 4 days in open air at room temperature.
Figure 41:
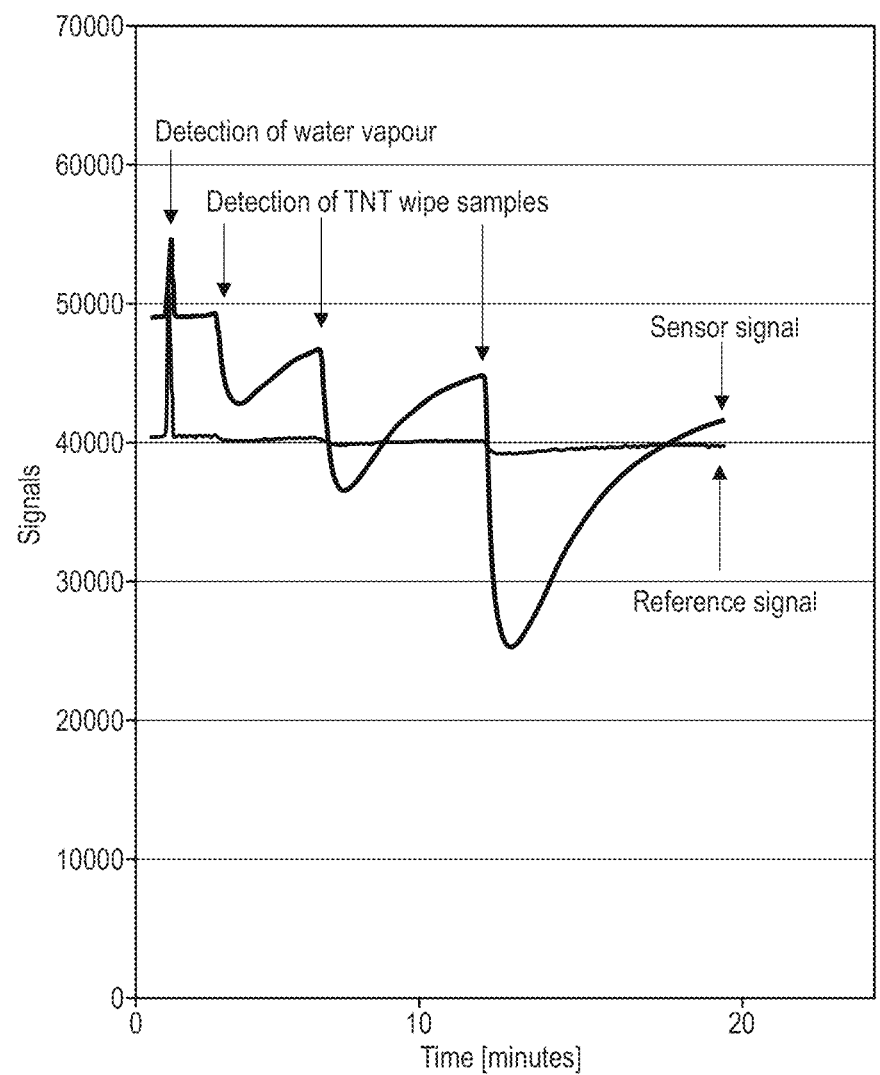
FIG. 41 shows, in a dual measurement system, in which the sensor material SM1 and the corresponding reference material are wetted uniformly with analyte in the hand-held device, the changes to the fluorescence signals in the presence of water vapour and TNT. The increase in the fluorescence signal (left) of the sensor material SM1 and of the corresponding reference material caused by vaporisation of a drop of water at the measurement head of the hand-held device heated to 150° C. can be seen. When heating three TNT wipe samples of different concentration at the measurement head of the hand-held device, the fluorescence signal of the sensor material SM1 firstly decreases in 18 seconds to 13-44% and increases again in the regeneration phase. The reference material by contrast demonstrates a maximum fluorescence quenching of 2% with heating of the three TNT wipe samples.
Figure 42:
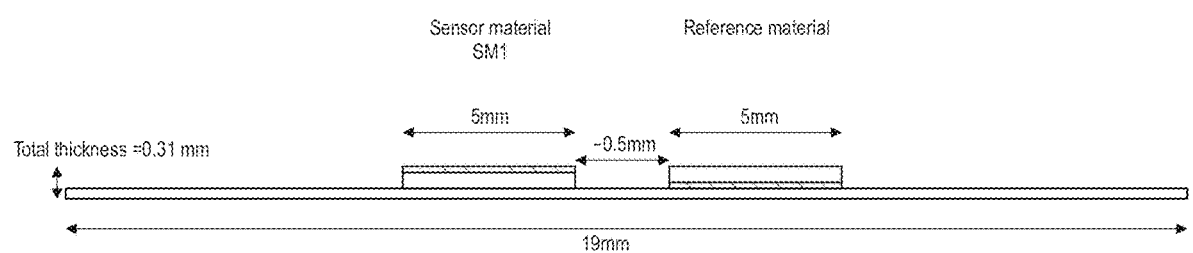
FIG. 42 shows the sensor material SM1 on a glass substrate (Ø 5 mm, 0.13 mm layer thickness), which was glued to a glass substrate (Ø 19 mm, 0.13 mm layer thickness) using an optical adhesive. The corresponding reference material was located between a Ø 5 mm and a Ø 19 mm glass substrate (0.13 mm layer thickness).

FIG. 38 shows the signal of the sensor material SM1 in the hand-held device before and after the measurement of 3 μL aqueous samples without and with TNT (1.18 mg/L, c=5.2 μM), which are vaporised with the measurement head of the hand-held device heated to 150° C. When measuring pure water, a fluorescence quenching is observed that reverts back to the starting state. In the case of TNT-contaminated samples, a fluorescence quenching is also initially observed, wherein, however, as the signal regenerates it drops further to the 5% TNT detection limit once the starting state has been reached. In order to avoid contamination of the hand-held device by water samples, the measurements can also be taken above the aqueous TNT sample (1.18 mg/L, c=5.2 μM). Compared to the water samples, a fluorescence intensification caused by high amounts of water on the sensor material is not observed. The fluorescence quenching caused by TNT reaches the 5% TNT detection limit in 32 seconds and reaches the 10% TNT detection limit in 58 seconds. (FIG. 39).

Proceeding from the present results, the fluorescent molecules described here are adsorbed on the polymer. In the result of the achieved state, a NOx compound can reversibly subtract an electron from the triphenylamino group of the probe on the polymer surface and can quench the fluorescence thereof. The sensitivity of the detection is dependent here on the layer thickness of the molecular probe in the polymer film and on the absorption capacity of the polymer of the particular explosive. Depending on its volatility, the explosive can be desorbed again, since the fluorescence response is reversible. This means that the polymer adsorbs the explosive or increases the dwell time thereof in the vicinity of the probe and enables the subtraction of an electron from the receptor unit triphenylamine.

In accordance with the embodiments proposed here as a whole, a probe concept has been developed, wherein a reversible physico-chemical interaction of a NOx compound at a detection reagent preferably comprising a triphenylamine leads to a signal profile of a fluorescence of the detection reagent that can be measured by spectroscopy. In accordance with the embodiments proposed by way of example, the embedding of the fluorescence probes in a polymer matrix, for example in a polymer matrix comprising poly(benzyl methacrylate), poly(benzyl acrylate), polystyrene or poly(ethylene glycol dimethacrylate)/poly(2-hydroxyethyl methacrylate) for the detection of non-volatile explosives, such as TNT and poly(1,4-bisacryloylpiperazine) and derivatives thereof, poly(1,4-bisacryloylpiperazine)/poly(2-hydroxyethylmethacrylate) or poly(ethylene glycol dimethacrylate)/ poly(2-hydroxyethyl methacrylate) for the detection of the marker substance DMDNB is also proposed. This embedding makes it possible to perform the detection by means of fluorescence spectroscopy of TNT in the dissolved, solid or gaseous state, even in mixed phases, simultaneously. Due to the use of poly(1,4-bisacryloylpiperazine), even very small amounts of the marker DMDNB from the air can be enriched in the pores of the polymer matrix and at the same time detected using the molecular probe. For regeneration of the fluorescence optical properties of the analyte-sensitive layer, a defined amount of water (1 µL to 2 µL) is vaporised at the measurement head heated to 150° C. and then forces the analyte (explosive, marker) from the polymer pores. Once the water has evaporated from the polymer pores, the emission signal measured by the measuring apparatus increases quickly and reaches the starting value again. An internal referencing is also proposed, which makes it possible to increase the reliability of the assay.

For detection of the explosives in air or as a wipe sample, the analyte-sensitive layer is exposed in the measuring apparatus to a heated air flow, wherein the (heated) air inlet is held against the sample or against a wipe sample. To this end, a suitable measurement head, comprising an air inlet can be heated for example to a temperature >150° C. When the detection limit is reached in a specific period of time under known ambient influences (humidity and temperature), the presence of a NOx compound is indicated as fluorescence quenching of the analyte-sensitive layer. As a result of the combined use of various specific analyte-sensitive layers (for example SM3 for the marker substance DMDNB), the composition of the corresponding explosive can be narrowed down. Additional information regarding the volatility of the particular analyte can be obtained by means of measuring the regeneration period of the measurement signal. The analyte-sensitive layer can then be regenerated at higher temperature and optionally additionally with water vapour. The use of water significantly reduces the waiting time in the case of SM3 (previously contaminated with the marker DMDNB) until a new measurement (see FIG. 28). The water vapour conducted by means of the measurement head onto the analyte-sensitive layer forces analyte from the polymer layer. The analyte-sensitive layer is regenerated by being fully dried, which is evident on the basis of a full re-establishment of the characteristic fluorescence of the particular detection reagent.

The suitability for use of previously known AFPs as molecular probes for NOx explosives is extremely limited under practical measurement conditions, apart from a few exceptions. One reason for this is constituted by full siphon positive results in the case of humidity changes and a resultant high false alarm rate. This is attributed particularly to the self-quenching effect of the hydrophobic SFPs on account of the fact that they move closer together in the presence of water. Only a small number of sensors is therefore known that can detect the explosives in the air, as wipe samples, and from water and organic solvent samples at the same time. Further sensors that are responsive to nitrogen oxide are based on the thermal decomposition of the explosives as wipe samples and NOx compounds. Besides the irreversible nature of this reaction, the low selectivity is disadvantageous however and significantly limits the practicability of this detection method under local conditions.

The need for a simple and inexpensive detection method for NOx explosives independently of the particular ambient conditions is therefore still very high.

Indicator substances—such as those proposed here—have the advantage compared to AFPs that they in principle are very selective and cross-sensitivities can be minimised. The disadvantage is generally an inadequate broadband detection.

In accordance with the above-describe principles, the cross-sensitivity of analyte-sensitive layers for explosives and marker substances based on NOx is reduced. Furthermore, more information regarding the composition of a sample, comprising at least one explosive and optionally at least one marker substance, is attained on the basis of a fluorescence-based optical measurement.

The selectivity and the sensitivity with respect to the explosive and the stability of the particular analyte-sensitive layer are adjustable under the measurement conditions by means of the molecular structure, the layer thickness, and the thickness of a polymer film carrier material of the proposed detection reagents. They also can be controlled by means of the chemical nature of the particular polymer material and the precise composition and molecular layer structure of the analyte-sensitive layer structure on the substrate.

Advantages of the proposed embodiments, in particular of the sensor materials SM1-SM4, are the inexpensive and simple synthesis of the respective molecular probes. The production of the polymer films is reproducible without difficulty (i.e. can be standardised) in high numbers by the described methods and is possible inexpensively. The detection method itself is sensitive and delivers reliably quantitative details regarding the concentration of the particular NOx compound in the examined sample (air, water, organic solvent, solid materials). It makes it possible to obtain results quickly and therefore can be used for local analysis in the interest of safety and environmental protection.

As described above, explosives and markers based on NOx can be reliably detected with the detection reagents or molecular probes 4, 5 and 6 depending on the polymer material as carrier of these probes. The immobilisation of the probe described here on the corresponding polymer film ensures a photostability and air stability of the sensor layer in a temperature range of 0-130° C. for the first time. The high stability of the sensor layers makes it possible to also measure samples from organic solvents and water. Providing a highly sensitive fluorescence probe for determining TNT in groundwater is of direct practical significance, for example for health and consumer protection.

The described fluorescence indicators (detection reagents) based on triarylamine, with their high quantum yield, possibility for excitation over a broad spectrum, high photostability, air stability and long-term stability, and a pronounced insensitivity to ambient influences (such as changes in the humidity, the presence of organic and/or aqueous solvent vapours and oxygen), are suitable on the corresponding carrier materials, comprising non-fluorescent, apolar polymer films, for the detection of explosives based on NOx units, for the detection of thermal decomposition products of explosives such as nitrogen oxides, starting materials for producing explosive materials such as nitric acid, and for the detection of marker substances such as DMDNB and DNT.

In accordance with the above-described exemplary embodiments and under consideration of the findings presented here, it is proposed to use probes 4 and 5 on poly(benzyl methacrylate), poly(benzyl acrylate) and polystyrene polymer films for the qualitative and quantitative detection of the non-volatile explosives TNT, tetryl, RDX, HMX, PETN, ammonium nitrate and the marker substance 2,4-dinitrotoluene. It is also proposed to use probes 5 and 6 on polymer films, comprising poly(1,4-bisacryloylpiperazine) and derivatives and mixed films thereof, comprising poly(1,4-bisacryloylpiperazine)/poly(2-hydroxyethyl methacrylate) for the qualitative and quantitative detection of the marker substance DMDNB. It is also proposed to use probe 5 on mixed films, comprising poly(ethylene glycol dimethacrylate)/poly(2-hydroxyethyl methacrylate) for the qualitative and quantitative detection of TNT and of DMDNB.

The triphenylamine motif of detection reagents 4, 5 and 6 is used for the detection of nitro compounds, wherein the stability of the dye at the polymer-air boundary is dependent on the composition of the polymer. The polymer additionally also controls the dwell time of the particular explosive on the polymer surface and thus the interaction between molecular probe and analyte (explosive). After calibration, the quenching of the fluorescence signal of the analyte-sensitive layer under the influence of the explosive bonded to the receptor unit is used for the quantitative determination of said explosive in the air, in aqueous and organic solution, and on wipe samples. The regeneration of the fluorescence signal of the analyte-sensitive layer occurring for example under the action of water vapour can also be used alone for the identification of a previously adsorbed fluorescence-quenching analyte, or can be consulted in a supplementary manner if an unknown NOx-containing analyte is to be determined.

In particular, the following embodiments are proposed in accordance with the invention.

1. A detection reagent for an analyte comprising a NOx group, wherein the detection reagent comprises an aryl amine and a structural formula of the aryl amine is selected from structural formulas 1, 2 or 3:

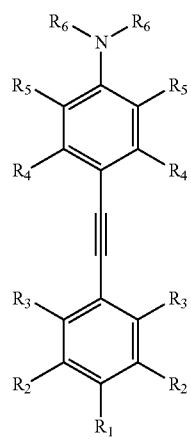
(1)

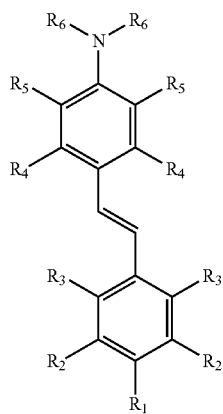
(2)

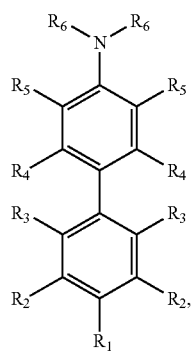
(3)

wherein
$R_1$ is selected from $CO_2^-$, $PhCO_2^-$, $CO_2X$ or $PhCO_2X$ with X=H, alkyl, vinyl, allyl, homoallyl or aryl or
$R_1$ stands for $C(O)NX_2$ or $PhC(O)NX_2$, with X=H, alkyl, perfluoroalkyl, vinyl, allyl, homoallyl or aryl;
$R_2$, $R_3$, $R_4$, and/or $R_5$ independently of one another are selected from H, F, an alkyl or an aryl; and
$R_6$ is selected from an alkyl and an aryl.

2. The detection reagent according to embodiment 1, wherein the aryl amine has structural formula 1 and $R_1$ stands for a carboxylic acid alkyl ester, aryl carboxylic acid alkyl ester, or for a N,N'-dialkylamide, aryl-N,N'-dialkylamide.

3. The detection reagent according to embodiment 1 or 2, wherein $R_2$, $R_3$, $R_4$ and $R_5$ stand for H.

4. The detection reagent according to any one of the preceding embodiments, wherein $R_6$ stands for a phenyl group and the aryl amine thus comprises a triphenylamine motif.

5. The detection reagent according to embodiment 4, wherein the triphenylamine motif is covalently bonded to a phenyl group in at lest one para position, and remaining para positions are unsubstituted or methylated.

6. The detection reagent according to embodiment 5, wherein the triphenylamine motif and the phenyl group are linked by means of a triple bond, by means of a double bond, or by means of a single bond.

7. The detection reagent according to embodiment 4, wherein the structural formula of the aryl amine is selected from structural formulas 4, 5 and 6:

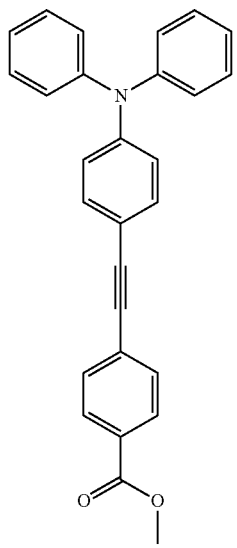
(4)

-continued

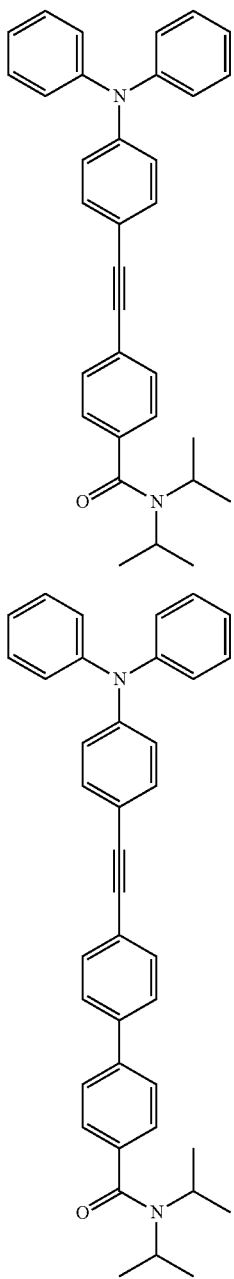

(5)

(6)

wherein the triphenylamine motif gives up an electron as donor to the NOx group of the analyte or receives an electron as receptor from the NOx group of the analyte, with a quenching of the fluorescence of the detection reagent being measurable if the electron is given up to the NOx group of the analyte, and/or with a regeneration of fluorescence being measurable if the electron is received, such that the analyte can be qualitatively and/or quantitatively determined optically.

8. The detection reagent according to embodiment 7, wherein the analyte comprising the NOx group is selected from: TNT, DNT, tetryl, PETN, NG, EGDN, DNDMB, ammonium nitrate, RDX and HMX.

9. The detection reagent according to any one of the above embodiments, wherein the analyte comprising the NOx group is present in a sample comprising an organic solution, an aqueous solution, a mixed organic-aqueous solution, an air sample, and/or a wipe sample.

10. A method for detecting an analyte comprising a NOx group, comprising the following steps:
providing an analyte-sensitive layer, comprising a polymer film on a carrier material and a detection reagent according to any one of embodiments 1 to 9 adsorptively bound to the polymer film;
interacting the analyte comprising the NOx group with the analyte-sensitive layer;
measuring a fluorescence property of at least a portion of the analyte-sensitive layer.

11. The method according to embodiment 10, further comprising:
heating and/or vaporising a defined sample volume, which potentially contains the analyte comprising the NOx group;
conducting a gas or gas mixture, comprising the heated or vaporised defined sample volume, to the analyte-sensitive layer, such that the analyte comprising the NOx group is enriched in and/or on the analyte-sensitive layer;
determining the composition and/or concentration of the analyte comprising the NOx group with use of stored measurement data of a comparative measurement.

12. The method according to embodiment 10 or 11, further comprising the step of:
regenerating the analyte-sensitive layer by contact with a NOx-free fluid, by bake-out and/or by incident flow with water vapour.

13. The method according to any one of embodiments 10 to 12, wherein the fluorescence property is selected from:
a fluorescence quantum yield, a fluorescence lifetime; a fluorescence intensity, in particular from a fluorescence quenching or a fluorescence increase after a previous fluorescence quenching.

14. The method according to any one of embodiments 10 to 13, wherein the measurement of the fluorescence property comprises a direct detection of an electrical signal of at least one detector or a forming of a quotient from electrical signals which are detected at different excitation wavelengths by at least one detector.

15. The method according to any one of embodiments 10 to 14, wherein the fluorescence property is measured using a portable measuring device, preferably a portable measuring device that can be managed using one hand, and the measuring device comprises a scanning apparatus, which is designed to measure the fluorescence property at least at one fixed wavelength.

16. The method according to any one of embodiments 10 to 15, wherein the polymer film
has a thickness of from 1 nm to 5 nm and/or
has a surface concentration of the detection reagent of 30-75 µmol/cm² substrate.

17. The method according to any one of embodiments 10 to 16, wherein the analyte is an explosive.

18. The method according to any one of embodiments 10 to 17, wherein the polymer film comprises a polymer that is selected from: poly(benzyl methacrylate); poly(benzyl acrylate); polystyrene; a poly(aryl acrylate); a polyacrylamide; a polymer comprising alkyl-substituted aryl acrylates; poly(benzyl methacrylate)/polystyrene; poly(1,4-bisacryloylpiperazine) and derivatives of poly(1,4-bisacryloylpiperazine); poly(1,4-bisacryloylpiperazine)/ poly(2-hydroxyethylmethacrylate); and/or poly(ethylene glycol dimethacrylate)/poly(2-hydroxyethyl methacrylate).

19. The method according to any one of embodiments 10 to 18, further comprising the step of:
    complexing the detection reagent by polymer chains of the polymer film at a polymer-air interface and/or enriching the analyte comprising the NOx group by the polymer film.

20. A production method for an analyte-sensitive layer, comprising the steps of:
    providing a substrate;
    constructing a polymer film on the substrate;
    applying a detection reagent according to any one of embodiments 1 to 9 to the constructed polymer film, wherein the analyte comprises a NOx group.

21. The production method according to embodiment 20, wherein the substrate, on its surface, has at least one kind of functional groups which can be used after a chemical activation to anchor the polymer film on the substrate.

22. The production method according to embodiment 20 or 21, wherein the provided substrate has a flat surface, for example is a plate, and the polymer film is constructed at least on portions on one side and/or at least in portions on both sides.

23. The production method according to embodiment 20 or 21, wherein the substrate has a curved surface at least in portions and surrounds a cavity which has at least one inlet opening for feeding the analyte and at least one outlet opening for discharging the analyte, wherein the polymer film is constructed on a substrate surface located in the cavity.

24. The production method according to any one of embodiments 20 to 23, wherein the application is performed by at least partial wetting and/or spraying, such that the detection reagent is adsorbed on the polymer film.

25. The production method according to embodiment 24, wherein the at least partial wetting and/or spraying is performed by a spin coater, a spray coater, a piezoelectric metering system, a printer, a nanoplotter, an inkjet printer, or a stamp.

26. The production method at least according to any one of embodiments 20 to 25, wherein the substrate is selected from: a polymer, a metal, a flat glass or a glass tube, a ceramic, or at least one of the specified materials.

27. The production method according to at least one of embodiments 20 to 26, wherein the construction of the polymer film on the substrate comprises the steps of:
    activating the substrate;
    applying a solution of the polymer in a solvent;
    covalently bonding the dissolved polymer to the activated substrate;
    separating the solvent.

28. An analyte-sensitive layer for an analyte comprising a NOx group, comprising a substrate, a polymer layer arranged on the substrate and at least one detection reagent adsorbed on the polymer layer, wherein a fluorescence intensity of the detection reagent in the presence of the analyte is reduced compared to a fluorescence intensity of the detection reagent in the absence of the analyte.

29. The analyte-sensitive layer according to embodiment 28, wherein the polymer film constructed on the substrate has a plurality of zones comprising different detection reagents, such that the analyte-sensitive layer has portions of different sensitivity for different analytes comprising a NOx group.

30. An analyte-sensitive layer according to any one of embodiments 28 or 29, wherein
    the polymer film comprises at least one layer of a hydrophobic polymer, comprising individual covalently bonded polymer chains, wherein the covalently bonded polymer chains comprise on average from 18 to 26, typically from 20 to 24, preferably 22±1 benzyl methacrylate units,
    the analyte comprising the NOx group is selected from TNT, DNT, tetryl, PETN, NG, EGDN, $NH_4NO_3$, RDX and HMX.

31. Use of a detection reagent according to any one of embodiments 1 to 9 and/or of a method according to any one of embodiments 10 to 19 and/or of an analyte-sensitive layer according to embodiments 28 to 30 to monitor a limit value of an explosive.

The described embodiments can be combined arbitrarily with one another. Although specific embodiments have been presented and described herein, it lies within the scope of the present invention to suitably modify the shown embodiments, without departing from the scope of protection of the present invention. The following claims are a first, non-binding attempt to define the invention generally.

REFERENCES

[1] Xu F., Peng L., Orita A., Otera J. (2012) Dihalo-Substituted Dibenzopentalenes: Their Practical Synthesis and Transformation to Dibenzopentalene Derivatives. Org. Lett. 14, 3970-3973;

[2] Schröder N., Wencel-Delord J., Glorius F. (2012) High-Yielding, Versatile, and Practical [Rh(III)Cp*]-Catalyzed Ortho Bromination and Iodination of Arenes. J. Am. Chem. Soc. 134, 8298-8301;

[3] Yang Y-S., Swager T. M. (1998) Fluorescent Porous polymer Films as TNT Chemosensors: Electronic and Structural Effects. J. Am. Chem. Soc. 120, 11864-11873;

[4] Yang Y-S., Swager T. M. (1998) Porous Shape Persistent Fluorescent polymer Films: An Approach to TNT Sensory Materials, J. Am. Chem. Soc. 120, 5321-5322;

[5] Sanchez J. C., Trogler W. C. J. (2008) Efficient Bluewithting Silafluorene-fluorene-conjugated Copolymers: Selective Turn-off/Turn-on Detection of Explosives. Mater. Chem., 18, 3143-3156;

[6] Che Y., Gross D. E., Huang H., Yang D., Yang X., Discekici E., Xue Z., Zhao H., Moore J. S., Zang L., (2012) Diffusion-Controlled Detection of Trinitrotoluene: Interior Nanoporous Structure and Low Highest Occupied Molecular Orbital Level of Building Blocks Enhance Selectivity and Sensitivity. J. Am. Chem. Soc. 134, 4978-4982;

[7] Thomas III, S. W.; Amara J. P., Bjork R. E., Swager T. M. (2005) Amplifying Fluorescent polymer Sensors for the Explosives Taggant 2,3-Dimethyl-2,3-dinitrobutane (DMNB). Chem. Commun., 4572-4574;

[8] Mardelli M., Olmsted J. (1977) calorimetric Determination of the 9,10-Diphenyl-Anthracene Fluorescence Quantum Yield. Journal of Photochemistry, 7, 277-285;

The invention claimed is:

1. A detection reagent for an analyte comprising a NOx group, wherein the detection reagent comprises an aryl amine having structural formula:

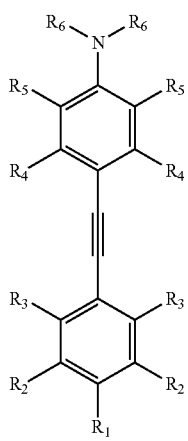

(1)

wherein

R₁ is selected from $CO_2X$ or $PhCO_2X$ with X=vinyl, allyl, homoallyl or aryl or R₁ stands for $C(O)NX_2$ or $PhC(O)NX_2$, with X=H, alkyl, perfluoroalkyl, vinyl, allyl, homoallyl or aryl;

R₂, R₃, R₄, and R₅ stand for H; and

R₆ is an aryl.

2. A detection reagent for an analyte comprising a NOx group, wherein the detection reagent comprises an aryl amine having structural formula:

(1)

wherein

R₁ stands for $C(O)NX_2$ or $PhC(O)NX_2$, with X=H or alkyl;

R₂, R₃, R₄, and/or R₅ independently of one another are selected from H, F, an aryl; and R₆ is an aryl.

3. A detection reagent for an analyte comprising a NOx group, wherein the detection reagent comprises an aryl amine, wherein the structural formula of the aryl amine is selected from structural formulas 4, 5 and 6:

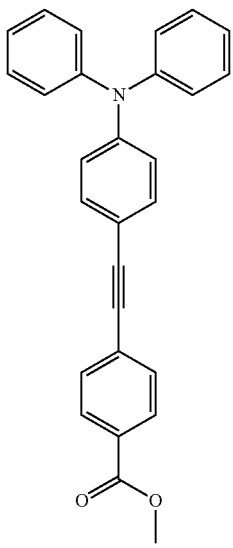

(4)

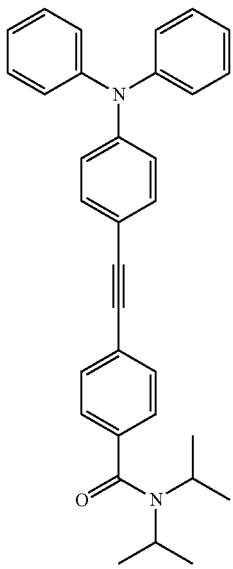

(5)

-continued

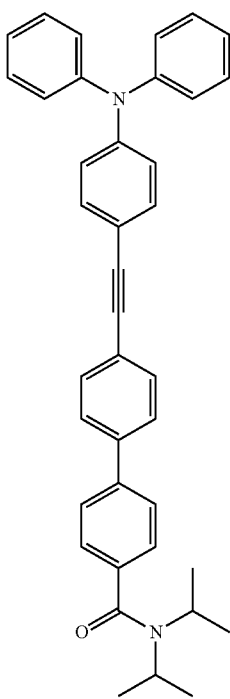

(6)

4. The detection reagent according to claim 3, wherein the analyte comprising the NOx group is selected from: TNT (2,4,6-trinitrotoluene), DNT (2,4-dinitrotoluene or 2,6-dinitrotoluene), tetryl (2,4,6-trinitrophenylmethylnitramine), PETN (pentaerythritol tetranitrate), NG (nitroglycerin), EGDN (ethylene glycol dinitrate), DNDMB (2,3-dimethyl-2,3-dinitrobutane), ammonium nitrate, RDX (hexahydro-1,3,5-trinitro-1,3,5-triazine) and HMX (octahydro-1,3,5,7-tetranitro-1,3,5,7-tetrazocine).

5. An analyte-sensitive layer for an analyte comprising a NOx group, comprising
a substrate,
a polymer layer arranged on the substrate and
at least one detection reagent adsorbed on the polymer layer,
wherein the at least one detection reagent comprises a detection reagent according to claim 1, and
wherein a fluorescence intensity of the detection reagent in the presence of the analyte is reduced compared to a fluorescence intensity of the detection reagent in the absence of the analyte.

6. The analyte-sensitive layer according to claim 5, wherein the polymer layer arranged on the substrate has a plurality of zones comprising different detection reagents, such that the analyte-sensitive layer has portions of different sensitivity for different analytes comprising a NOx group.

7. An analyte-sensitive layer according to claim 5, wherein
the polymer layer comprises at least one layer of a hydrophobic polymer, comprising individual covalently bonded polymer chains, wherein the covalently bonded polymer chains comprise on average from 18 to 26 benzyl methacrylate units, and
the analyte comprising the NOx group is selected from TNT, DNT, tetryl, PETN, NG, EGDN, NH$_4$NO$_3$, RDX and HMX.

8. A method for detecting an analyte comprising a NOx group, comprising the following steps:
providing an analyte-sensitive layer comprising a polymer film on a carrier material and a detection reagent according to claim 1, the detection reagent adsorptively bound to the polymer film;
interacting the analyte comprising the NOx group with the analyte-sensitive layer; and
measuring a fluorescence property of at least a portion of the analyte-sensitive layer.

9. The method according to claim 8, further comprising:
heating and/or vaporising a defined sample volume, which contains the analyte comprising the NOx group;
conducting a gas or gas mixture, comprising the heated and/or vaporised defined sample volume, to the analyte-sensitive layer, such that the analyte comprising the NOx group is enriched in and/or on the analyte-sensitive layer;
determining the composition and/or concentration of the analyte comprising the NOx group with use of stored measurement data of a comparative measurement.

10. The method according to claim 8, further comprising the step of:
regenerating the analyte-sensitive layer by contact with a NOx-free fluid, by bake-out and/or by incident flow with water vapour.

11. The method according to claim 8, wherein the fluorescence property is selected from:
a fluorescence quantum yield, a fluorescence lifetime; a fluorescence intensity; or a fluorescence increase after a previous fluorescence quenching.

12. The method according to claim 8, wherein the measuring the fluorescence property comprises detection at different excitation wavelengths by at least one detector.

13. The method according to claim 8, wherein the fluorescence property is measured using a portable measuring device that is manageable using one hand, and the measuring device comprises a scanning apparatus, which is designed to measure the fluorescence property at least at one fixed wavelength.

14. The method according to claim 8, wherein the polymer film
has a thickness of from 1 nm to 5 nm and/or
has a surface concentration of the detection reagent of 30-75 μmol/cm$^2$.

15. The method according to claim 8, wherein the analyte is an explosive.

16. The method according to claim 8, wherein the polymer film comprises a polymer that is selected from: poly (benzyl methacrylate); poly(benzyl acrylate); polystyrene; a poly(aryl acrylate); a polyacrylamide; a polymer comprising alkyl-substituted aryl acrylates; poly(benzyl methacrylate)/polystyrene;
poly(1,4-bisacryloylpiperazine) and derivatives of poly(1,4-bisacryloylpiperazine);
poly(1,4-bisacryloylpiperazine)/poly(2-hydroxyethylmethacrylate); and/or poly(ethylene glycol dimethacrylate)/poly(2-hydroxyethyl methacrylate).

17. The method according to claim 8, further comprising the step of:
complexing the detection reagent to polymer chains of the polymer film at a polymer-air interface and/or enriching the analyte comprising the NOx group with the polymer film.

18. The method according to claim 8, wherein
the polymer film comprises at least one layer of a hydrophobic polymer, comprising individual covalently bonded polymer chains, wherein the covalently bonded polymer chains comprise on average from 18 to 26 benzyl methacrylate units, and the analyte comprising the NOx group is selected from TNT, DNT, tetryl, PETN, NG, EGDN, $NH_4NO_3$, RDX and HMX.

19. A production method for an analyte-sensitive layer for an analyte comprising a NOx group, comprising the steps of:
providing a substrate;
constructing a polymer film on the substrate; and
applying a detection reagent according to claim 1 to the constructed polymer film.

20. The production method according to claim 19, wherein a surface of the provided substrate has at least one kind of functional group which can be used after a chemical activation to anchor the polymer film to the substrate.

21. The production method according to claim 19, wherein the provided substrate has a flat surface, and the polymer film is constructed at least on portions of one side of the substrate and/or at least on portions of two sides of the substrate.

22. The production method according to claim 19, wherein at least a portion of the substrate has a curved surface and the substrate surrounds a cavity which has at least one inlet opening for feeding the analyte and at least one outlet opening for discharging the analyte, wherein the polymer film is constructed on a substrate surface located in the cavity.

23. The production method according to claim 19, wherein the applying is performed by at least partial wetting and/or spraying, such that the detection reagent is adsorbed on the polymer film.

24. The production method according to claim 23, wherein the at least partial wetting and/or spraying is performed by a spin coater, a spray coater, a piezoelectric metering system, a printer, a nanoplotter, an inkjet printer, or a stamp.

25. The production method at least according to claim 19, wherein the substrate is selected from: a polymer, a metal, a flat glass, a glass tube, and a ceramic.

26. The production method according to claim 19, wherein the constructing the polymer film on the substrate comprises the steps of:
activating the substrate;
applying a solution of the polymer in a solvent;
covalently bonding the dissolved polymer to the activated substrate; and
removing the solvent.

27. A method for detecting an analyte comprising a NOx group, comprising the following steps:
providing an analyte-sensitive layer comprising a polymer film on a carrier material and a detection reagent according to claim 2, the detection reagent adsorptively bound to the polymer film;
interacting the analyte comprising the NOx group with the analyte-sensitive layer; and
measuring a fluorescence property of at least a portion of the analyte-sensitive layer.

28. A production method for an analyte-sensitive layer for an analyte comprising a NOx group,, comprising the steps of:
providing a substrate:
constructing a polymer film on the substrate; and
applying a detection reagent according to claim 2 to the constructed polymer film.

29. A method for detecting an analyte comprising a NOx group, comprising the following steps:
providing an analyte-sensitive layer comprising a polymer film on a carrier material and a detection reagent according to claim 3, the detection reagent adsorptively bound to the polymer film;
interacting the analyte comprising the NOx group with the analyte-sensitive layer; and
measuring a fluorescence property of at least a portion of the analyte-sensitive layer.

30. A production method for an analyte-sensitive layer for an analyte comprising a NOx group, comprising the steps of:
providing a substrate:
constructing a polymer film on the substrate: and applying a detection reagent according to claim 7 to the constructed polymer film.

* * * * *